(12) United States Patent
Kramer et al.

(10) Patent No.: US 12,262,887 B2
(45) Date of Patent: Apr. 1, 2025

(54) SYSTEMS, DEVICES AND METHODS FOR TISSUE FIXATION AND APPROXIMATING TISSUE DEFECTS

(71) Applicant: TAS Medical Inc., Windermere, FL (US)

(72) Inventors: Thomas A. Kramer, San Carlos, CA (US); Albert K. Chin, Palo Alto, CA (US); Gannon Borchers, San Francisco, CA (US); Peter Bugos, Redwood City, CA (US); Andrew Kwok, Belmont, CA (US); Steven Ledbetter, San Carlos, CA (US)

(73) Assignee: TAS Medical, Inc., San Carlos, CA (US)

( * ) Notice: Subject to any disclaimer, the term of this patent is extended or adjusted under 35 U.S.C. 154(b) by 0 days.

(21) Appl. No.: 18/233,633

(22) Filed: Aug. 14, 2023

(65) Prior Publication Data
US 2023/0389918 A1    Dec. 7, 2023

Related U.S. Application Data

(63) Continuation of application No. 17/753,887, filed as application No. PCT/US2020/053148 on Sep. 28, 2020, now Pat. No. 11,793,508.
(Continued)

(51) Int. Cl.
*A61B 17/06* (2006.01)
*A61B 17/00* (2006.01)
*A61B 17/68* (2006.01)

(52) U.S. Cl.
CPC ............ *A61B 17/06166* (2013.01); *A61B 2017/00004* (2013.01); *A61B 2017/00871* (2013.01);
(Continued)

(58) Field of Classification Search
CPC .... A61B 17/06166; A61B 2017/00004; A61B 2017/00871; A61B 2017/06176; A61B 2017/681
See application file for complete search history.

(56) References Cited

U.S. PATENT DOCUMENTS

| 3,570,497 A | 3/1971 | Lemole |
| 4,119,091 A | 10/1978 | Partridge |

(Continued)

FOREIGN PATENT DOCUMENTS

WO    2016/205834 A1    12/2016

OTHER PUBLICATIONS

Communication pursuant to Rule 164(1)/Supplementary Search Report issued by the European Patent Office in application No. 20870077.3, dated Sep. 15, 2023.
(Continued)

*Primary Examiner* — Phong Son H Dang
(74) *Attorney, Agent, or Firm* — Knobbe, Martens, Olson & Bear, LLP

(57) ABSTRACT

A medical device for approximating and securing tissue without requiring knots includes a lock-head, a strap section, distal protuberance, and a leader section. The device also includes a transition section between the leader and the strap section and a stiffening section proximal to the protuberance. The leader section is used to draw the strap section into the body through small apertures in tissue and the transition section provides a gradual transition in stiffness and size between the leader and the strap section.

32 Claims, 33 Drawing Sheets

Related U.S. Application Data

(60) Provisional application No. 62/907,577, filed on Sep. 28, 2019.

(52) U.S. Cl.
CPC ............... *A61B 2017/06176* (2013.01); *A61B 2017/681* (2013.01)

(56) References Cited

U.S. PATENT DOCUMENTS

| | | | |
|---|---|---|---|
| 4,535,764 A | | 8/1985 | Ebert |
| 4,813,416 A | | 3/1989 | Pollak et al. |
| 4,950,285 A | | 8/1990 | Wilk |
| 5,318,566 A | | 6/1994 | Miller |
| 5,456,246 A | | 10/1995 | Schmieding et al. |
| 5,549,619 A | | 8/1996 | Peters et al. |
| 5,636,412 A | | 6/1997 | Lodi et al. |
| 5,741,283 A | | 4/1998 | Fahy |
| 6,050,998 A | | 4/2000 | Fletcher |
| 8,572,813 B2 | * | 11/2013 | Monaco ............... G09F 3/037 40/665 |
| 8,696,692 B2 | | 4/2014 | Hoglund |
| 9,047,788 B2 | * | 6/2015 | Koh ............... G09F 3/037 |
| 9,055,940 B2 | | 6/2015 | Chin |
| 9,439,746 B2 | | 9/2016 | Bell et al. |
| D769,704 S | * | 10/2016 | Nitta ............... D8/387 |
| 9,474,553 B2 | * | 10/2016 | Koch ............... A61B 17/844 |
| 9,585,705 B2 | | 3/2017 | Koch et al. |
| 9,611,083 B2 | * | 4/2017 | Schuttler ............ B65D 63/1027 |
| 9,751,670 B2 | * | 9/2017 | Williams ........... B65D 63/1072 |
| 10,366,632 B1 | * | 7/2019 | Tropper ................. G09F 3/037 |
| 10,702,260 B2 | | 7/2020 | Sengun et al. |
| 11,213,284 B2 | | 1/2022 | Chin et al. |
| 11,337,704 B2 | | 5/2022 | Kaneda |
| 11,344,295 B2 | | 5/2022 | Gustafson |
| 11,357,660 B2 | | 6/2022 | O'Connor et al. |
| 2003/0236538 A1 | | 12/2003 | Aikens |
| 2004/0059357 A1 | | 3/2004 | Koseki |
| 2004/0068292 A1 | | 4/2004 | Koseki |
| 2005/0288674 A1 | * | 12/2005 | Golobek ............ A61B 17/8861 606/74 |
| 2006/0276809 A1 | | 12/2006 | Oliveira |
| 2007/0055258 A1 | | 3/2007 | Hansen |
| 2009/0062851 A1 | | 3/2009 | Rosenblatt |
| 2012/0041441 A1 | | 2/2012 | Bernstein et al. |
| 2015/0157327 A1 | | 6/2015 | Hoglund |
| 2018/0116778 A1 | | 5/2018 | Chin et al. |
| 2019/0192142 A1 | | 6/2019 | Dumanian |
| 2019/0365364 A1 | | 12/2019 | Chin et al. |

OTHER PUBLICATIONS

Chavez-Cartaya et al, "Adjustable Nylon Ties for Abdominal Wall Closure", The American Journal of Surgery, vol. 163, Jun. 1992, 4 pages.

International Search Report and Written Opinion, issued in PCT/US2020/053148, dated Dec. 22, 2020.

Notification Concerning Transmittal of International Preliminary Report on Patentability and International Prelminary Report on Patentability issued in PCT/US2020/053148, mailed Apr. 7, 2022.

* cited by examiner

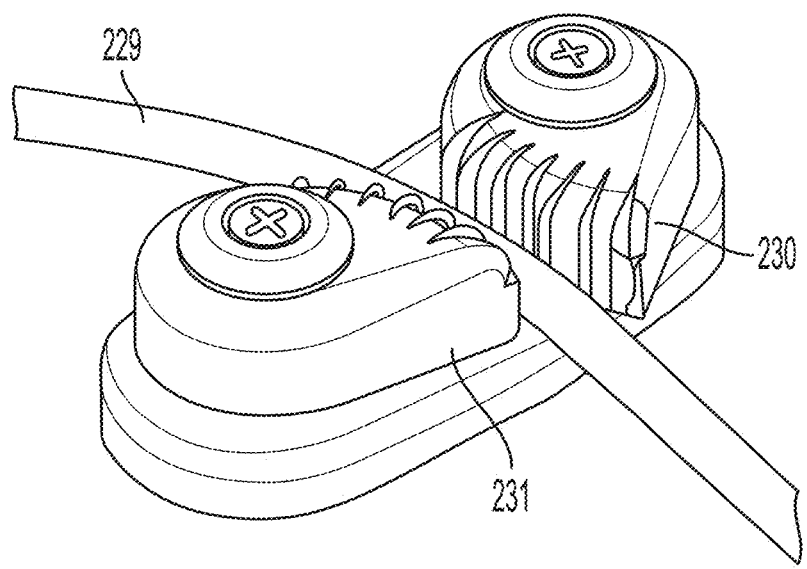
FIG. 26
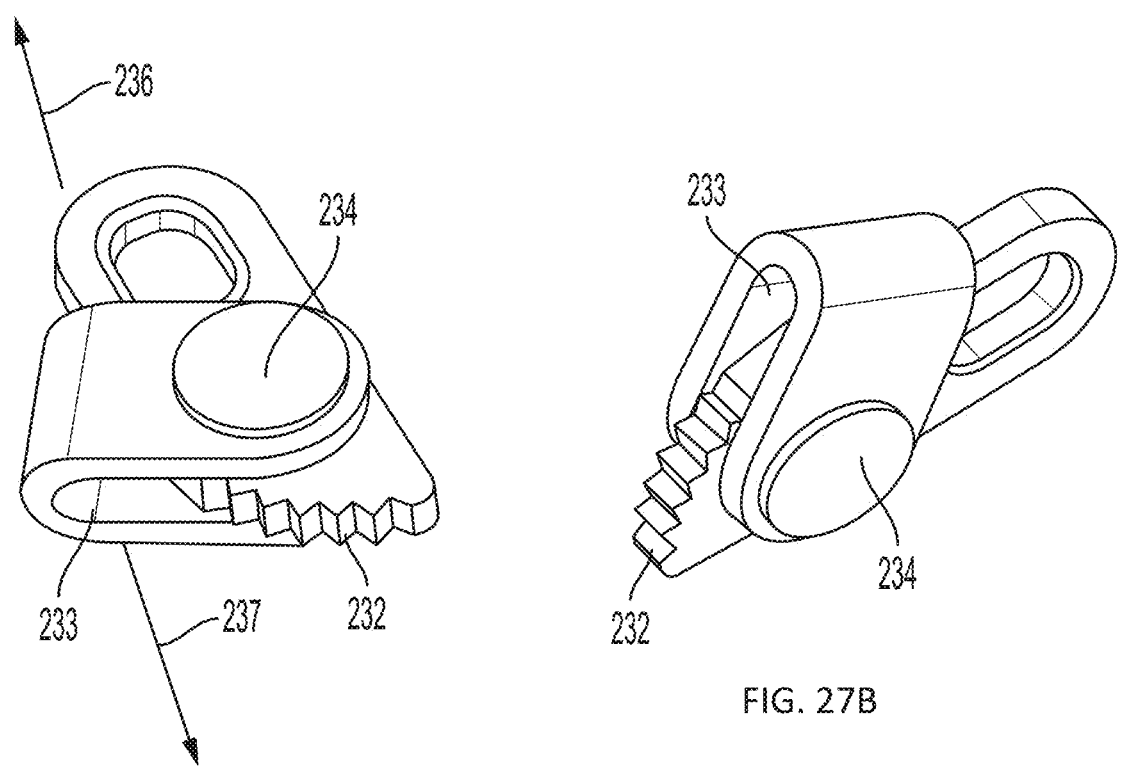
FIG. 27A
FIG. 27B

SYSTEMS, DEVICES AND METHODS FOR TISSUE FIXATION AND APPROXIMATING TISSUE DEFECTS

CROSS-REFERENCE TO RELATED APPLICATIONS

This application is a continuation of U.S. application Ser. No. 17/753,887 filed Mar. 17, 2022 which is a 371 of PCT Application No. PCT/US2020/053148, filed Sep. 28, 2020 and also claims priority to U.S. Provisional Patent Application No. 62/907,577, filed Sep. 28, 2019, the entire contents of which are incorporated herein by reference.

TECHNICAL FIELD

This disclosure relates to medical devices and methods, and more specifically, straps having one-way locking (knotless) characteristics for approximating tissue such as in closing a hernia defect.

BACKGROUND

Sutures are commonly used to re-appose tissue and to hold the tissue in a desired configuration until it can heal together. Sutures initially provide the full strength of the repair, but then become mostly redundant as the tissue heals. Depending on the anatomical region where the sutures are deployed, there may be forces naturally acting to pull the tissues apart, which may delay or prevent healing. Conventional sutures provide a circular or single-point cross-sectional profile that does not effectively distribute force because they concentrate it much like slicing cheese by passing a taut wire through the relatively soft cheese material. Such limitations of sutures are common to many surgical applications, but particularly to repairs of large defects or other repairs involving large forces acting on the sutures such as in ventral hernias.

Ventral hernias are abdominal wall defects that generally occur following a breakdown in the closure of a previous abdominal open surgical midline incision. 350,000-500,000 ventral hernias are repaired annually in the United States. In these cases, the defect may be greater than 10 cm wide and 40 cm or more in length and extend below the xiphoid process of the sternum inferiorly to the pubic symphysis; they may be repaired via conventional "open" surgical methods requiring a large incision, or laparoscopic procedures requiring small abdominal incisions. Ventral hernias may arise after a patient undergoes abdominal surgery. For example, upon completion of an open abdominal surgical procedure, closure of the full thickness abdominal wall is performed. Interrupted sutures are placed through the anterior rectus sheath, the rectus muscle, and the posterior rectus sheath. Suture repair has a long-term failure rate of 41%-52%, leading to ventral hernia formation. Poor tissue strength, coupled with significant tension in the suture lines, leads to failure of the abdominal closure requiring hernia repair.

In conventional laparoscopic repair, multiple trocar ports are inserted to place a large patch of prosthetic mesh to cover the defect. This approach causes far less postoperative pain as compared to open methods because a large abdominal incision is avoided. However, the abdominal defect is generally not closed; rather, a large prosthetic patch is tacked onto the inner surface of the abdominal wall to cover the defect. Placement of a large piece of artificial material results in a high rate of postoperative complications such as seroma formation. The fluid loculation of the seroma then increases the potential for infection of the laparoscopically placed mesh, necessitating its removal plus antibiotic therapy. Bowel adhesions are also a potential complication due to the implantation of a large foreign body patch.

It is desirable to close the abdominal defect using a laparoscopic technique, either partially or completely, to significantly decrease the size of the prosthetic mesh patch needed to repair the ventral hernia or eliminate the use of a mesh patch at the discretion of the surgeon. U.S. Pat. No. 9,055,940, incorporated herein in its entirety, describes a system and technique that uses capture devices that puncture through the abdominal wall on both sides of the hernia defect and grasp the ends of a suture delivered into the abdominal cavity. One end of the suture is pulled out of the body, and a trapping device is tunneled subcutaneously from the first end of the suture to grasp and deliver the opposite end of the suture to the first puncture site. The suture may be tied at the first puncture site, and the knot inserted through the skin down to the level of the anterior rectus sheath, where it may be tensioned to close the hernia defect. This technique is repeated for each interrupted suture placed during ventral hernia closure. If a relatively close spacing of 2 cm is used between sutures to increase the strength of the repair, and a 30 cm long hernia defect is being closed, 14 interrupted sutures will be required. With wide defects, the sutures must be tensioned incrementally and sequentially to gradually re-appose the edges; otherwise, the suture may tear through the abdominal wall tissue. A slip knot composed of two half-hitches is typically used to allow sequential tensioning of an individual suture. Continuous tension must be maintained on all sutures during the cinching and closure process. This may be performed by applying a surgical clamp immediately proximal to each slip knot after each sequential tensioning step. However, this leads to an excessive number of surgical clamps in the operating field.

The aforementioned hernia defect closure technique is overly tedious. Placement of each interrupted suture involves at least twelve surgical manipulation steps that must be performed for each of the ten or more sutures placed in the patient.

A laparoscopic technique and instrumentation is desired to place multiple interrupted fastening devices on each side of a hernia defect and allow serial cinching of each device to re-appose the edges of the defect. Additionally, the devices should have a larger tissue contact area than conventional sutures to reduce or prevent the devices from incising, pulling out, or tearing through the tissue.

SUMMARY OF THE INVENTION

A medical device for approximating and securing tissue without requiring knots includes a lock-head, a strap section, distal protuberance, and a leader section. The device also includes a transition section between the leader and the strap section and a stiffening section proximal to the protuberance. The leader section is used to draw the strap section into the patient's through small apertures in tissue and the transition section provides a gradual transition in stiffness and size between the leader and the strap section. In some embodiments, a plurality of medical devices is provided, each of the plurality of medical devices comprising a transition section between the leader and the strap section and a stiffening section, and a lock-head for receiving the distal end of the strap that allows translational movement therethrough in one direction, but preventinng translation movement of the strap through the lock-head in the opposing direction. The plurality of medical devices may be used to secure and approximate a soft tissue defect, with a plurality of straps securing the soft tissue defects in spaced apart locations. In some embodiments, the resulting plurality of straps may be tightened to close or approximate the soft tissue defect. In some embodiments, the tightening of the plurality of straps may be done sequentially and in a series of tightening to incrementally approximate the soft tissue defect.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 26 illustrates a perspective cutaway view an embodiment of a dual cam lock-head.

FIG. 27A illustrates a perspective view of an embodiment of a single cam lock-head.

FIG. 27B illustrates a perspective view of an embodiment of a single cam lock-head.

DETAILED DESCRIPTION

Figure 1:
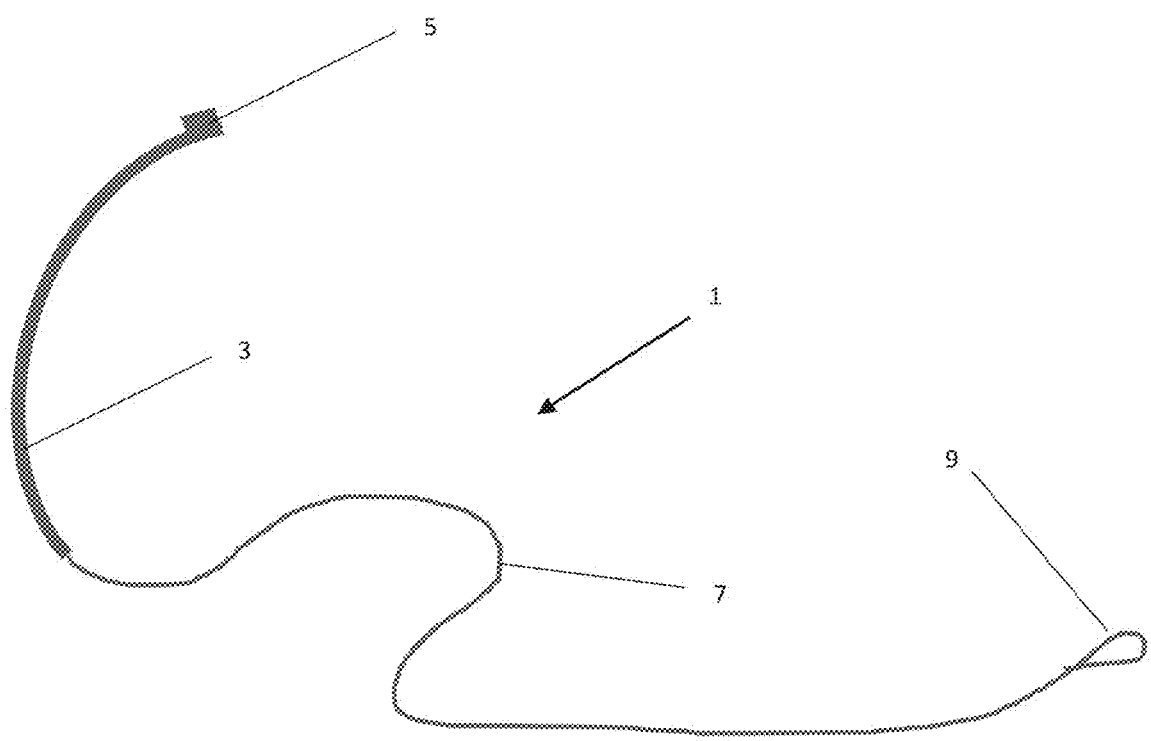
FIG. 1 illustrates an embodiment of a device for approximating tissue according to embodiments of the present disclosure.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

A description of example embodiments of the invention follows. Certain terminology is used in the following description for convenience and is not meant to be limiting. The words "proximally" and "distally" refer to directions toward and away from, respectively, the surgeon using the surgical instrument or device. The words "anterior," "posterior," "superior," "inferior" designate positions and orientations with respect to the human body.

A device and methods of manufacture of a surgical strap (the device) are presented here. At least part of the strap may be a permanent implant that holds a wound in the body, or it may be a temporary implant that, for example, holds skin like a suture to enable healing. Embodiments disclosed may be used to approximate any type of tissue in the body where sutures, wires, staples, or straps are used. Applications include approximating bone in orthopedics, such as in a sternotomy, hernia repair, and general wound closure. For illustrative purposes, the present disclosure describes the device and method in the context of hernia repair, and in particular, ventral hernia repair. However, the devices and methods presently disclosed may be used in any surgical procedure for joining tissue, closing a tissue opening or defect, or fastening a device to or between two or more sections of tissue.

With reference to FIG. 1, a first exemplary embodiment of a device 1 for closing a tissue opening is shown. The device comprises a lock-head 5 at a proximal end, a strap 3 emanating from the lock-head 5, and a leader 7 emanating from the strap 3. The leader 7 may have a loop 9 or other protuberance at its distal end to facilitate grasping during a surgical procedure; alternatively, the leader 7 may have a distal end without a grasping feature in some embodiments because the leader may be easily grasped by some surgical tools without an engagement feature on the end. In general, the leader 7 may be grasped anywhere along its length by any common tools used for grasping sutures, but it may be easier, faster, or more convenient to grasp a loop or other prominent feature at the distal end, depending on the procedure and surgical tools available. As the leader 7 is smaller in cross-section and/or outer diameter, than at least portions of the strap 3, a lower force is generally required to pull the leader 7 through multiple layers of tissue.

FIGS. 2A-2G illustrate embodiments of straps having features along the length of a strap to engage with a lock-head to permit travel in only one direction, that is in a locking fashion commonly referred to as a zip-tie or cable tie. The device 1 can be tightened as it encircles a section of tissue to be approximated, and the device will stay tensioned without the surgeon holding the device or requiring any knots. This is a critical feature of certain embodiments of the inventions described herein as it allows the surgeon to at least partially tighten device 1 while attending to other tasks. The surgeon may then return to the at least partially tightened device 1 and either continue with the tightening process and/or the remaining procedural steps. Thus, embodiments of the described inventions may be considered "knotless", e.g., no slip knots and/or "clampless", i.e., requiring no clamping to achieve the above. As will be described further infra, such an arrangement allows serial cinching or tightening of the device 1 which may be advantageous in several ways, including the reason mentioned above. In addition, when more than one strap 3 is required, each related device 1 and strap 3 may be at least partially tightened in succession, allowing the surgeon great flexibility in the cinching or tightening procedure.

Figure 2A:
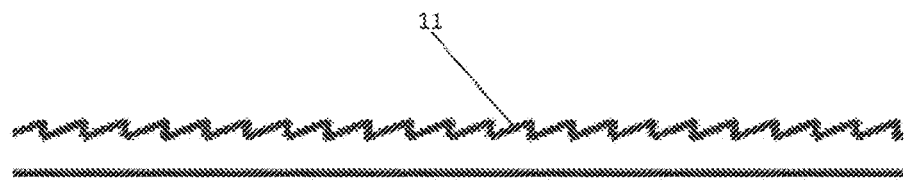
FIG. 2A illustrates a segment of an embodiment of a locking feature on a strap.

In one embodiment, the strap 13 may have opposing sides with ramped teeth 11 on one side and a relatively smooth opposing side, similar to a conventional zip tie, as shown in FIG. 2A.

Figure 2B:
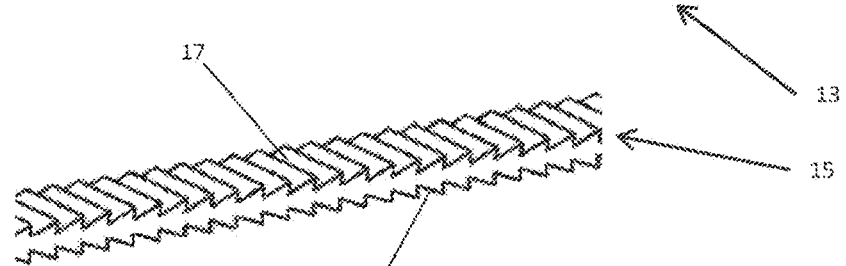
FIG. 2B illustrates a segment of an embodiment of a locking feature on a strap.

In another embodiment, the strap 15 may have teeth 17 and 18 on both opposing sides as in FIG. 2B. These teeth may be staggered (not shown) to avoid thin sections in the strap 15.

Figure 2C:
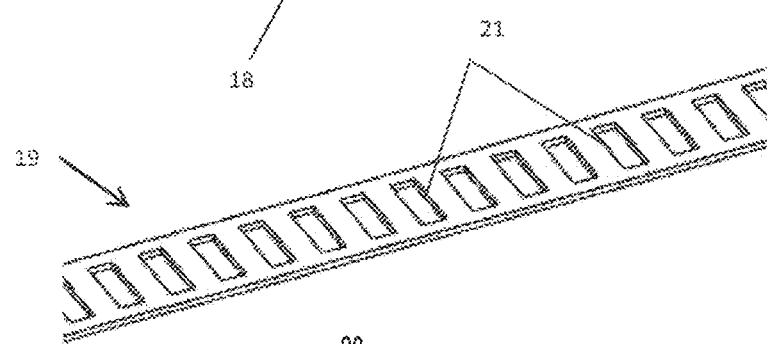
FIG. 2C illustrates a segment of an embodiment of a locking feature on a strap.

FIG. 2C illustrates an embodiment of a strap 19 with apertures 21 that engage with pawls or other features in a lock-head 5. This strap 19 may be easy to fabricate because the direction of the apertures 21 is orthogonal to the strap 19, so injection molding tooling may be relatively simple and low-cost. The apertures 21 may, in some embodiments, go entirely through the strap 19, or they may comprise pockets defined in the strap that do not extend through the strap 19, but have a thickness that is less than the thickness of the strap 19 as illustrated. In this embodiment, the locking head 5 will contain the features that enforce the one-way tightening motion or translation of the strap 19 through the locking head 5.

Figure 2D:
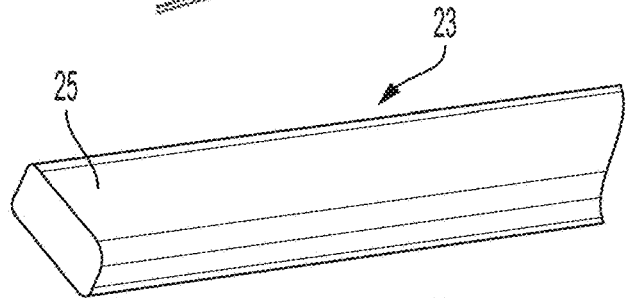
FIG. 2D illustrates a segment of an embodiment of a locking feature on a strap.

In some embodiments, the strap may lack discrete locking features. FIG. 2D illustrates such a strap 23 having a substantially smooth surface on at least one of the opposing sides that can engage with a lock-head that has teeth, a cam, tines, or other features that facilitate one-way locking by clawing, grasping, or gripping the strap using friction or otherwise impinging on the strap for grip. An elastomeric strap, e.g., may be smooth as shown in FIG. 2D. Some strap embodiments may be fully elastic or contain elastic elements and may continue to provide pressure to tissue as the tissue shrinks or otherwise relaxes after surgery. Elastic straps may be made of rubber-like materials such as thermoplastic elastomers (TPE's) or silicone.

Figure 2E:
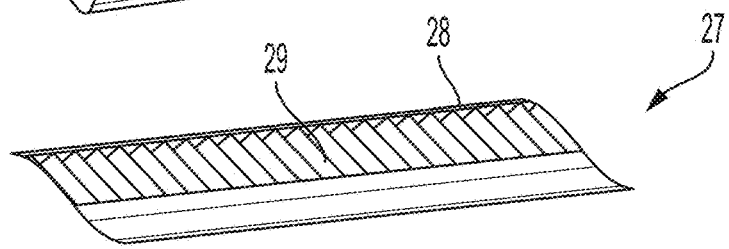
FIG. 2E illustrates a segment of an embodiment of a locking feature on a strap.

FIG. 2E shows another embodiment having side rails 28 on the opposite sides of the teeth 29 on at least one of the opposing sides of the strap 27. The side rails 28 add strength and stiffness to the strap 27. The side rails 28 may extend the length of the strap 27 or, alternatively, may extend along a section, or sections, of the strap 27.

Figure 2F:
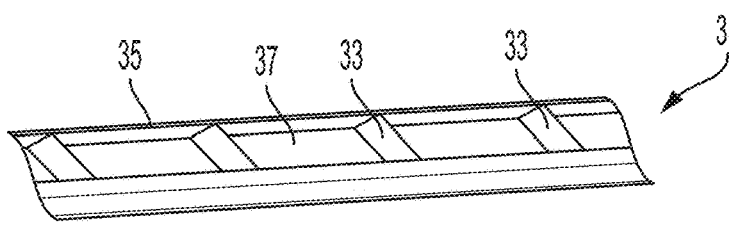
FIG. 2F illustrates a segment of an embodiment of a locking feature on a strap.

In some embodiments, the engagement features on the strap may have gaps. For example, FIG. 2F shows a strap 31 having teeth 33 separated by a gap 37, which may be a flat section or a void or a pocket as described above in connection with FIG. 2C; side rails 35 may also be included and as described in connection with FIG. 2E.

Figure 2G:
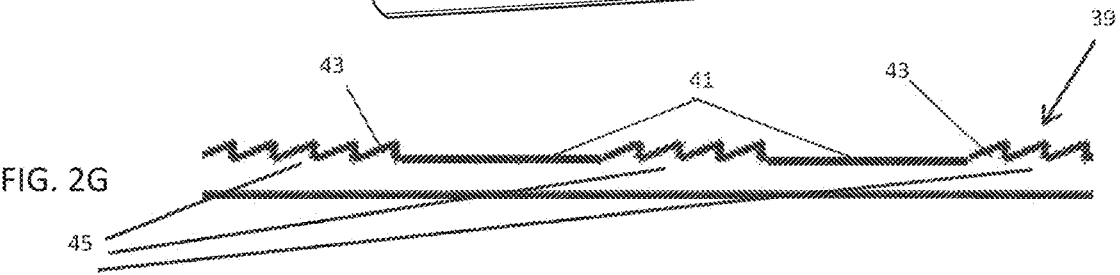
FIG. 2G illustrates a segment of an embodiment of a locking feature on a strap.

Other embodiments, including the embodiments disclosed above, may have multiple sets or sections of teeth 45 comprising one or more teeth 43, or other engagement features, separated or spaced longitudinally apart by gaps 41, as shown in FIG. 2G. This configuration allows the strap 39 to freely advance between toothed sections 43, having little resistance between spaced apart sections of teeth 45, so that it may be easily tightened without adding resistance when the strap is still loose on the anatomy. Furthermore, the gaps 41 also serve to reduce the number of impacts wherein individual strap teeth 43 contact a locking mechanism in a lock-head. For example, when the operator tightens a long strap, each tooth 43 on the strap 39 contacts the teeth in the lock-head, causing repetitive stress and potential wear on the teeth in the lock-head, which may reduce the holding strength of the lock-head. Therefore, intermittent tooth sections 45 reduce the number of contact incidences with the teeth 43 in the lock-head during tightening, possibly resulting in less wear and higher strength. Finally, the reduction of teeth on the strap may reduce the cost and complexity of manufacturing in processes such as injection molding because molding a long and narrow section of teeth, such as in a long zip tie, can require expensive tooling.

In some embodiments, there may be a section of teeth 45 having a longitudinal length followed by a gap and then one or more sections of teeth 45 also having a longitudinal length. The lengths of the sections of teeth 45 may be substantially equivalent or they may vary as the skilled artisan will understand. One exemplary length for the sections of teeth 45 may comprise approximately 25 mm, though the artisan will readily understand that other lengths may be implemented, each of which is within the scope of the present invention. This arrangement allows the surgeon to easily slide the strap 39 through the lock-head, then release the device when it engages a section of teeth 45, interprocedurally, so that the device will stay in place while the surgeon applies other self-locking devices to the wound. Next, the surgeon may cinch the strap further to engage the next spaced-apart set of teeth 45 at a tighter approximation (smaller perimeter) of the strap around the wound. The aforementioned approach is also possible with a strap having engagement features substantially all along its length. However, having a smaller section of engagement features or intermittent engagement sections may have manufacturing or cost advantages because the tooling required to make the features may be less complex.

The strap embodiments disclosed herein serve as examples, and one skilled in the art would recognize that there are many strap designs that provide one-way knotless and clampless locking capability when coupled with various lock-head designs, all of which are within the scope of the inventions disclosed herein. Furthermore, as the skilled artisan will now recognize, various combinations of the aforementioned embodiments are contemplated, for example, a strap 19 having apertures 21, as shown in FIG. 2C may also include side rails 28, similar to those in FIG. 2E.

Figure 3:
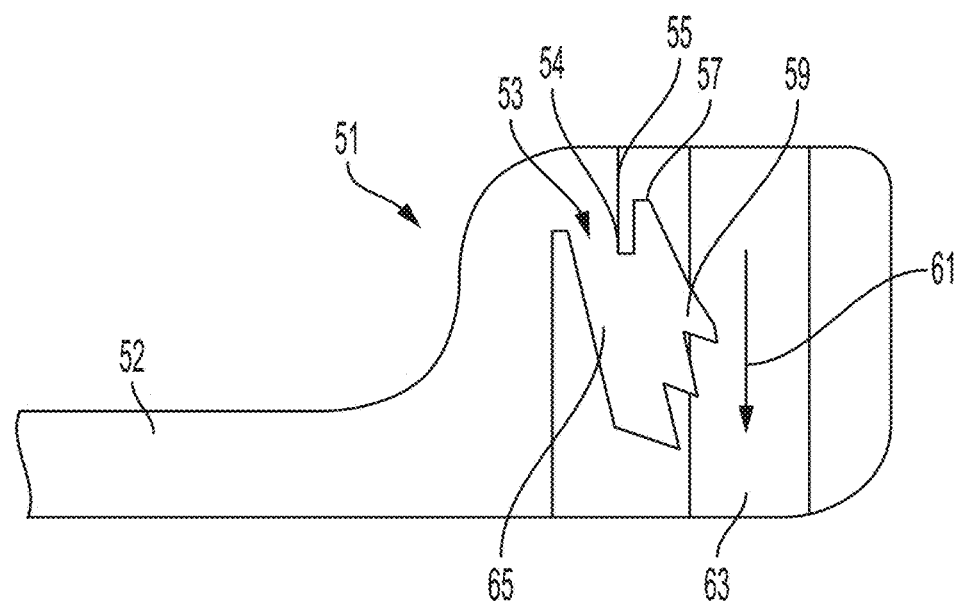
FIG. 3 illustrates a cross-sectional view of a lock-head embodiment.
Figure 4:
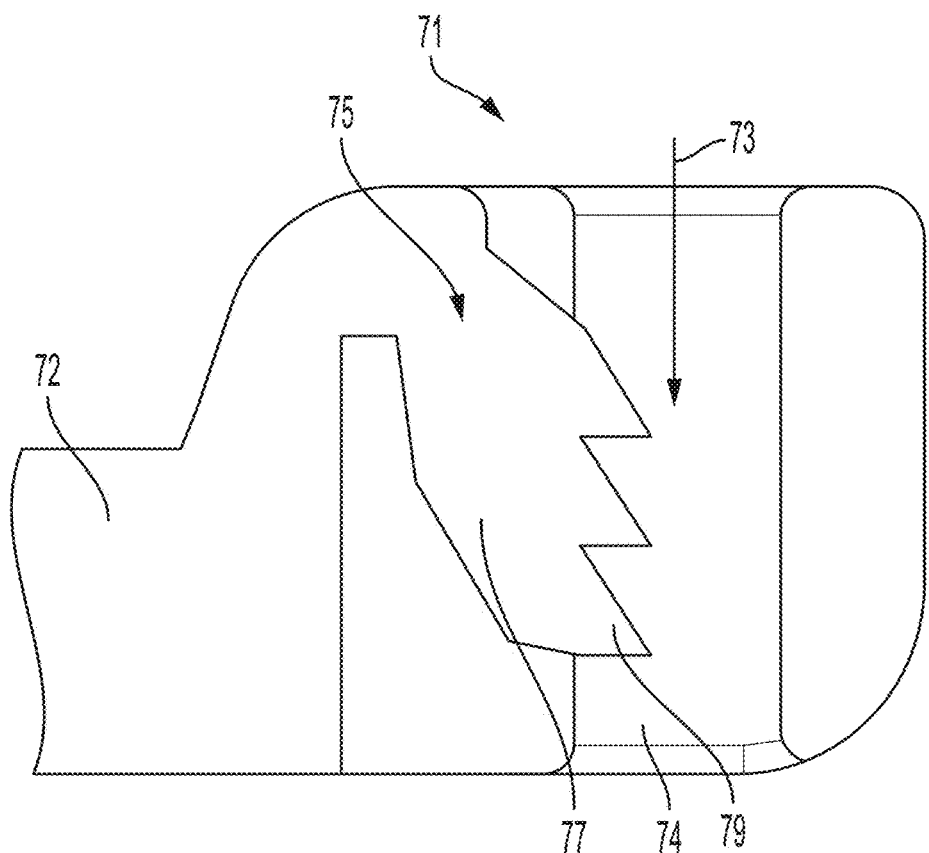
FIG. 4 illustrates a cross-sectional view of another embodiment of a lock-head.

Turning now to FIG. 3 through FIG. 7B where various examples of lock-heads are illustrated. FIG. 3 shows a cross-sectional view of lock-head 51 attached to the proximal end of a strap 52. The lock-head 51 has an elastic hinge 53 such that when the strap 52 (partially shown) passes through the channel 63 in the direction of the arrow 61, the pawl 65 deflects to allow the strap to pass through. When the strap 52 is pulled in the direction opposite of arrow 61, the teeth on the strap engage with the teeth 59 on the lock-head 51, thus preventing passage of the strap 52. When the strap is held in tension, the force of the strap 52 on the teeth 59 causes the pawl 65 to flex in the opposite direction about the apex 54 such that the teeth 59 tend to align with the strap 52 as it passes through the lock-head 51 causing more teeth 59 to engage with the teeth (not shown) on the strap 52 in the direction opposite arrow 61. In yet another embodiment, as shown in FIG. 4, a lock-head 71 has teeth 79 that are substantially parallel to the direction 73 that the strap 72 traverses. The elastic hinge 75 allows the pawl 77 to flex out of the way when the strap 72 passes through the channel 74 in the direction of the arrow 73, then flexing back to the orientation shown such that the teeth 79 are substantially parallel to the teeth on the strap allowing multiple teeth to engage with the strap (not shown).

Figure 5A:
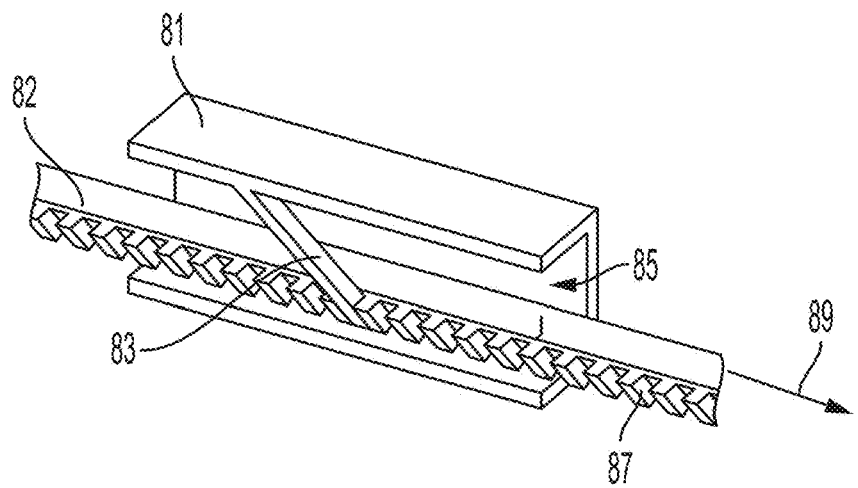
FIG. 5A illustrates a perspective view of a lock-head and strap embodiment.
Figure 5B:
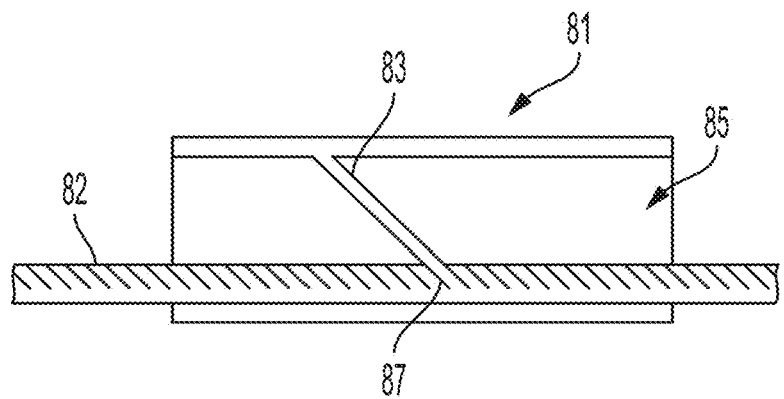
FIG. 5B illustrates a side cross-sectional view of a lock-head and strap embodiment.

FIGS. 5A and 5B illustrate a cross-sectional view of an embodiment of a lock-head 81 having a tab 83 that engages with gaps 87 in the strap 82. The tab 83 may be angled so that it allows the strap 82 to traverse through a channel 85 in the direction of the arrow 89 while preventing backward motion to achieve the one-way locking action. FIG. 5B shows another cross-sectional view of this embodiment wherein the tab 83 is engaged in a gap 87 in the strap 82. This embodiment of a lock-head 81 with one or more tabs 83 is generally compatible with strap designs having apertures such as that shown in FIG. 2C, i.e., cutouts or partial cutouts in the strap, although this type of lock-head is also compatible with toothed designs.

Figure 6:
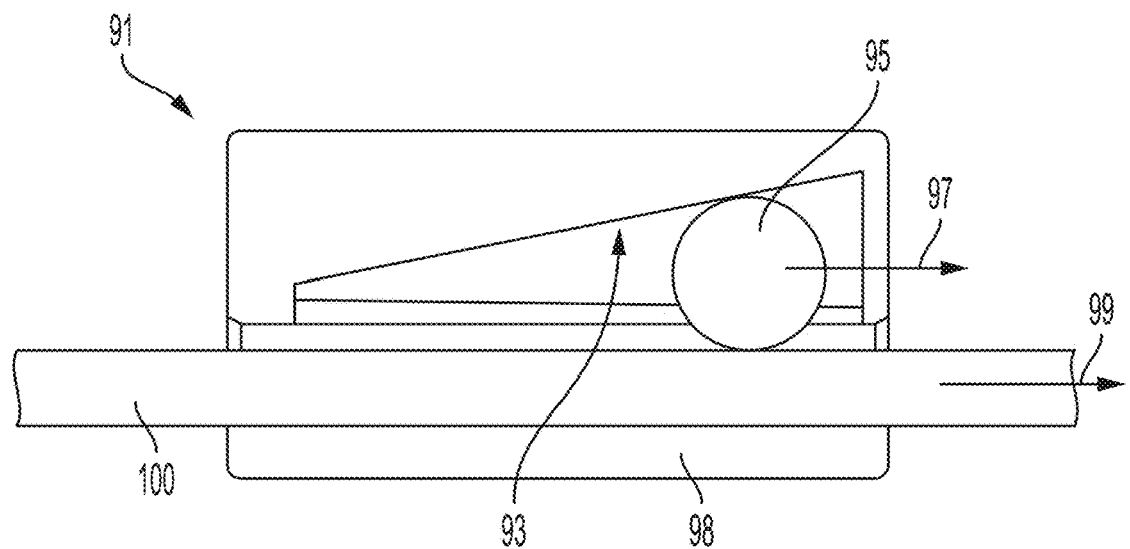
FIG. 6 illustrates a cross-sectional cutaway view of an embodiment of a lock-head comprising a ball.

The strap may use a ball and wedge to lock the strap, much like a clutch that may lock the strap with considerable force and with little or no backlash when transitioning from sliding to holding. FIG. 6 illustrates a lock-head 91 having a ball 95 captive between a sloped surface 93 and a strap 100. As the strap 100 is pulled in the tightening direction 99, the ball 95 displaces in the same direction 97 and away from the sloped face 93, allowing the strap 100 to translate freely. When the strap 100 is released by the operator, it is prohibited from traveling in the opposite direction because the ball 95 impinges on the sloped surface 93, which forces the ball 95 against the strap 100, thus clamping the strap 100 between the ball 95 and the bottom wall 98 of the lock-head 91. The ball 95 may instead be a cylinder in some embodiments to impart a line load rather than a point load on the strap 100, which may be smooth or textured, resulting in a relatively simple, low-cost strap. Indeed, this type of configuration may also be used with fabric, woven, or textile strap materials lacking discrete features to lock onto. Additionally, features to improve friction may be added to the strap 100 or the lock-head 91 where it contacts the strap 100, and including but not limited to exemplary straps shown in FIGS. 2C, 2D, 2F, 2G and 11B. Such features include, but are not limited to, surface roughness, texture, knurling, gratings, bumps, or ramped bumps.

Figure 7A:
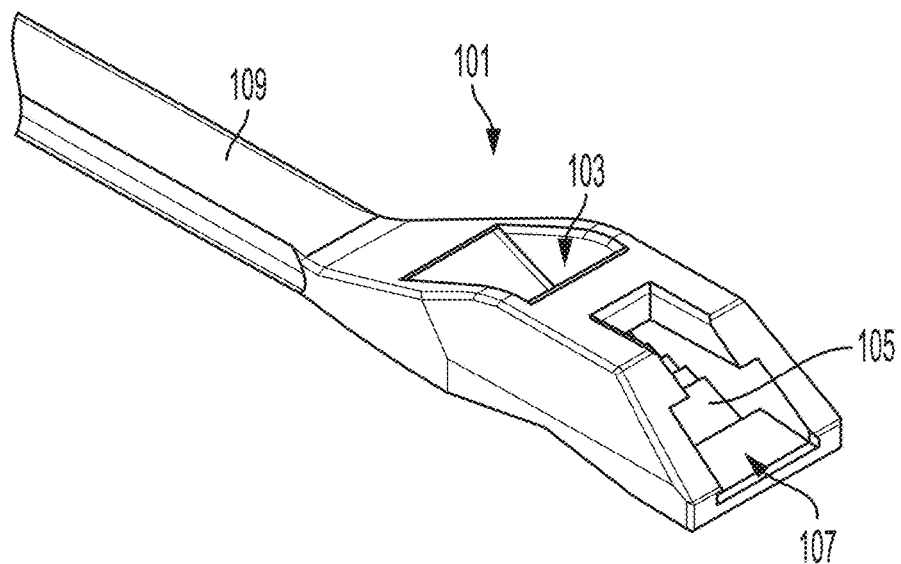
FIG. 7A illustrates a cross-sectional cutaway view of an embodiment of a low profile, in-line lock-head.
Figure 7B:
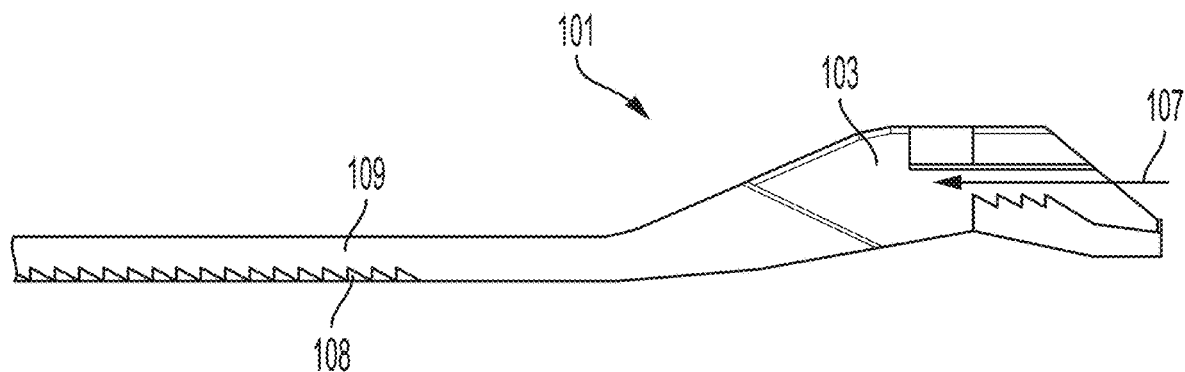
FIG. 7B illustrates a perspective cutaway view of an embodiment of a low profile, in-line lock-head.

An embodiment with a low-profile, in-line lock-head is shown in FIGS. 7A-B. The lock-head 101 has a channel 103 that is substantially parallel to the proximal portion of the strap 109 so that when the strap 109 passes through the lock-head 101 in the direction of the arrow 107, the distal strap (not shown) will reside substantially adjacent (e.g., parallel) to the proximal strap 109 (similar to the arrangement shown in FIG. 20B). In this configuration, the teeth 105 are relatively in-line with the proximal end of the strap 109, so that after the strap is inserted and cut, the remaining strap protruding through the channel 103 will be flush. As shown in the sectional view of FIG. 7B, the lock-head 101 may be low profile, which reduces trauma in the body and may reduce residual pressure on adjacent tissue; e.g., reducing skin bulging if the device resides near the skin.

The medical device embodiments disclosed herein may be comprised of different sections having disparate mechanical characteristics suitable for various aspects of a surgical procedure. For example, and with reference to FIG. 8, a device 1 is shown having different sections. The strap 3 is the section that transmits the force to approximate the tissue and remains in the body to hold the tissue together for an indefinite period of time. Therefore, the strap 3 has a size (diameter or width/thickness) and material composition to enable it to have enough tensile and bending strength to withstand the required insertion, approximation, and long-term holding loads. The leader 7 is long, highly flexible, and small in diameter; it is used to introduce the device into the body and pull the strap 3 along its path through tissue. As such, the leader 7 may be smoother, more flexible, or smaller in size as compared to the strap and as it transits through the body through a hole in the tissue, it may serve as a dilator to atraumatically pull the larger strap 3 through tissue without causing excessive resistance or damage to tissue. The device 1 may have a transition section 2 between the leader 7 and the strap 3 forming a gradual change in stiffness and size between the two sections of the device 1. The transition section 2 reduces the stress concentration inherent in connecting a relatively smaller member (the leader 7) to a relatively larger member (the strap 3) by acting as a strain relief. The transition section 2 may also reduce the stress incident on tissue as the strap 3 is pulled through the body preventing the device 1 from kinking as the leader 7 pulls the strap 3 through a tortuous path in the body through small anatomical pathways—this may also reduce the force required to pull the leader 7 into and out of the body because the device 1 will tend not to bind as the transition section 2 maneuvers around sharp corners. The distal end of the leader 7 may have a loop 9 to facilitate grasping the device 1 either from within the body or from outside of the body; the loop 9 may be stiffened, as described further below in this disclosure, to maintain an open shape during a procedure. In some embodiments, the leader 7 may have a stiffened portion 10 proximal to the loop 9 which, in these embodiments may or may not be stiffened. The stiffened portion 10 is stiff enough to retain a relatively rigid shape once inside the body cavity to facilitate grasping from within the body.

Figure 9A:
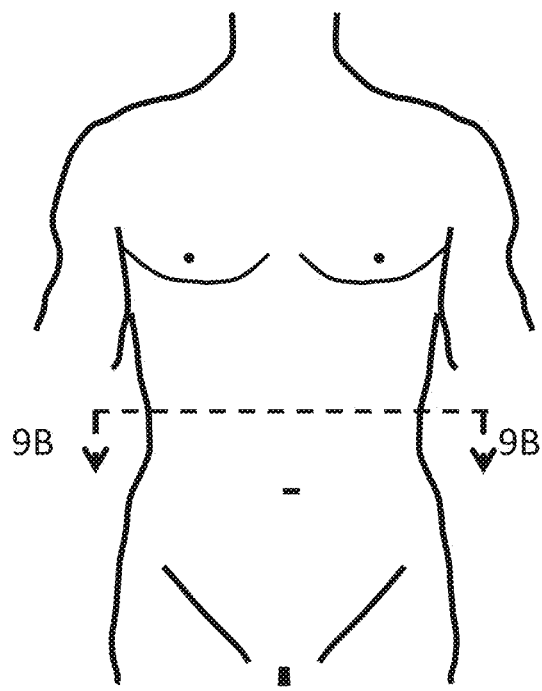
FIG. 9A illustrates a view of the anatomical location of a ventral hernia.
Figure 9B:
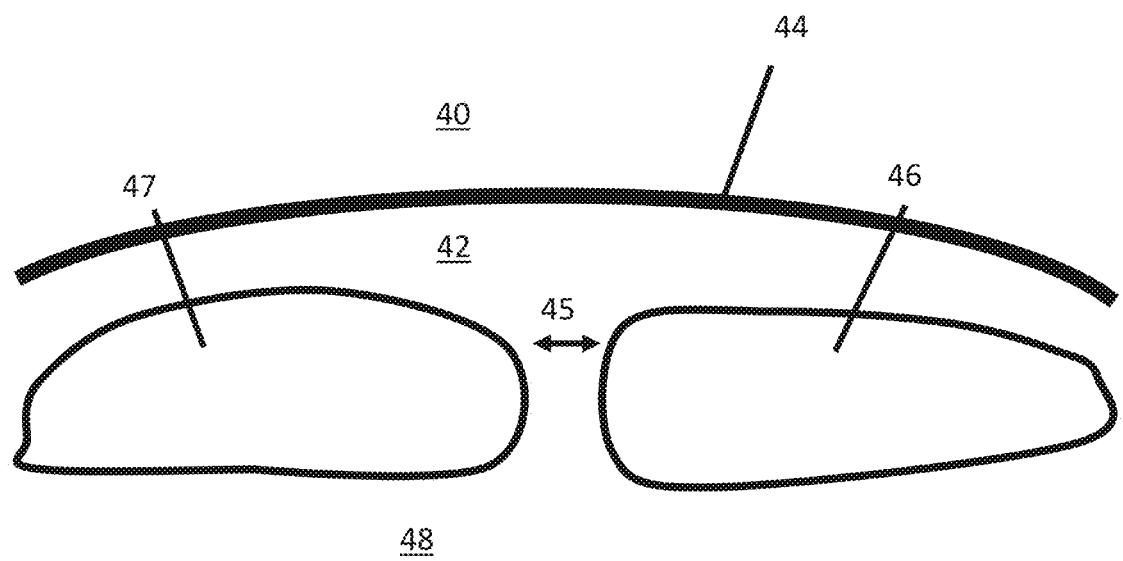
FIG. 9B illustrates a cross-sectional view of the anatomy of a ventral hernia.

To illustrate some of the features in the context of a surgery, an embodiment of the device is shown in the context of a ventral hernia procedure. The embodiments disclosed herein may be used in other surgical procedures that require approximating tissue, for example approximating muscle, fascia, skin, bone, and combinations thereof. FIGS. 9A-9B show a schematic of the anatomy of a ventral hernia. FIG. 9A shows a torso with a cross-section taken through the abdomen, which is shown in FIG. 9B, that will be used throughout this disclosure. The simplified anatomy of FIG. 9B shows skin 40, the right rectus abdominus muscle 46, the left rectus abdominus muscle 47, and an abdominal defect 45 residing between the abdominus muscles 46 and 47. Other regions of the body are also labeled for orientation, including the body cavity 48, the outside of body 40, and the subcutaneous region 42. For clarity, the figures do not show other types of tissue such as muscle, connective tissue, and fat; however, various tissue layers and anatomical features exist between the skin 44 and the body cavity 48.

Parts of a ventral hernia surgical procedure are illustrated herein to highlight the design and function of the device. More complete descriptions of ventral hernia procedures are described in commonly owned U.S. patent application Ser. No. 16/477,674 filed on Jul. 12, 2019, the entirety of which is incorporated herein by reference.

Figure 9C:
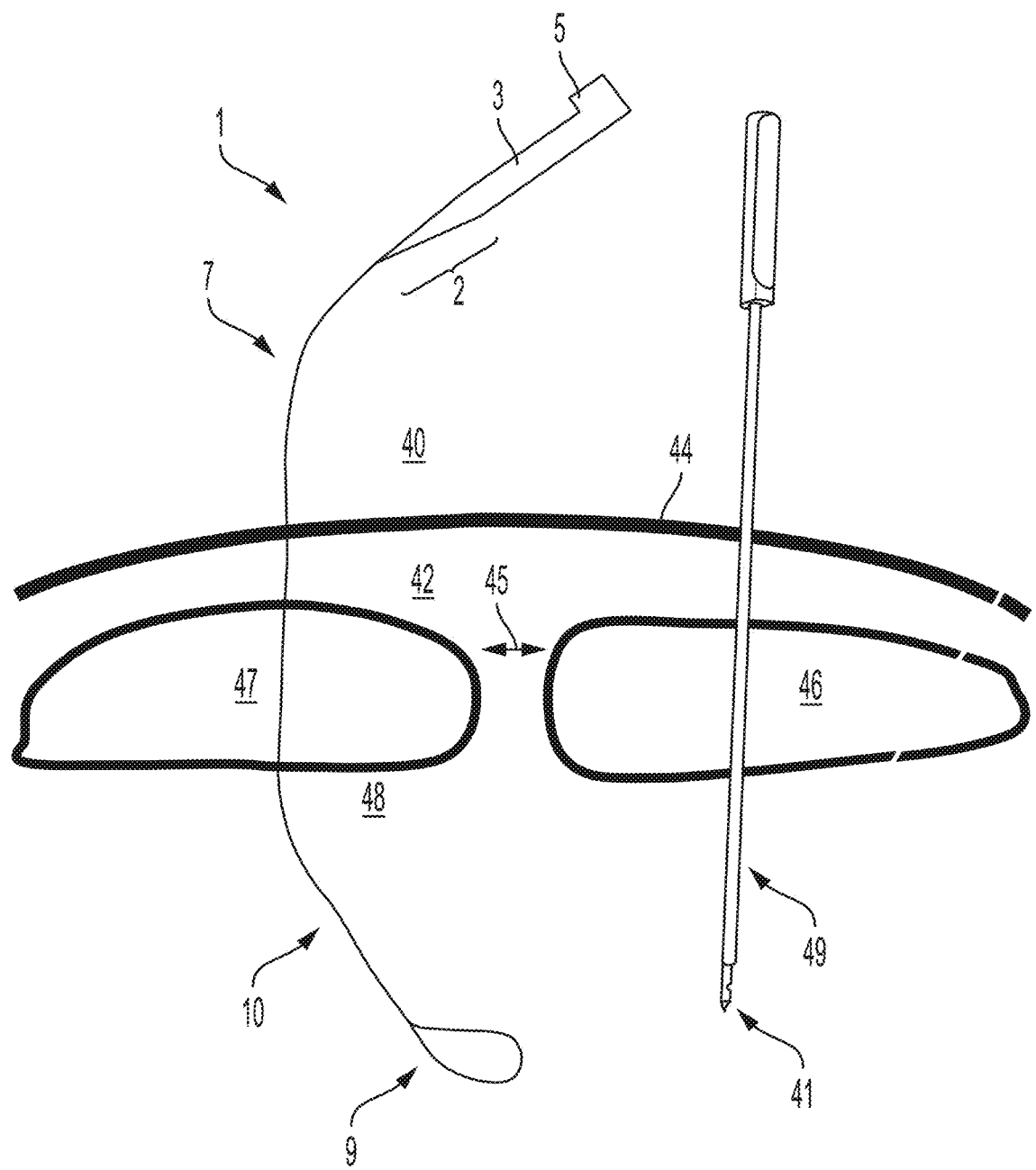
FIG. 9C illustrates steps in an exemplary ventral hernia procedure.

Now with reference to FIG. 9C, the device 1 is partially introduced into the body as part of a ventral hernia repair procedure. The leader has been placed into the body through a hole in the skin 44 and through the left rectus abdominus muscle 47 such that the loop 9 and the stiffened portion 10 reside inside of the body cavity 48. At this stage of an exemplar ventral hernia procedure, a grasping needle 49 has been inserted through the skin 44 and through the right rectus abdominus muscle 46 such that the tip 41 of the grasping needle 49 may engage with the loop 9 to pull the leader 7 out of the body. The increased stiffness of the loop 9 relative to the leader 7 provides some resistance to motion and deformation so that it may more easily be grasped. The wet surgical environment may cause a non-stiffened, or flaccid, loop 9 to collapse and/or close. Stiffening serves to keep this loop 9 open and available to the surgeon. The grasping needle 49 may be angled to directly reach the loop, or another surgical grasper such as a laparoscopic grasper, may be introduced into the body cavity to connect the loop 9 to the grasping needle 49.

The stiffened portion 10 of the leader 7 may also aid in grasping the loop 9. The stiffened portion 10 may have at least some bending stiffness so that it resists deforming when contacted so that a grasping tool will not push the leader 7 away excessively. Thus, the resistance of the stiffened portion 10 will tend to keep the loop in place rather than dangling in the body cavity loosely. Also, the wet surgical environment may cause a non-stiffened, or flaccid, leader 7 to adhere to nearby features such as the wall of the body cavity 48. Thus, the stiffened portion serves to keep the leader 7 and loop 9 presented and available to the surgeon. Furthermore, at least a portion of the stiffened portion 10 may be pre-bent or pre-curved relative to the leader 7 such that it resides toward the midline of the body for easier grasping. At least a portion of leader 7 may also be pre-curved as may be at least a portion of strap 3.

Figure 9D:
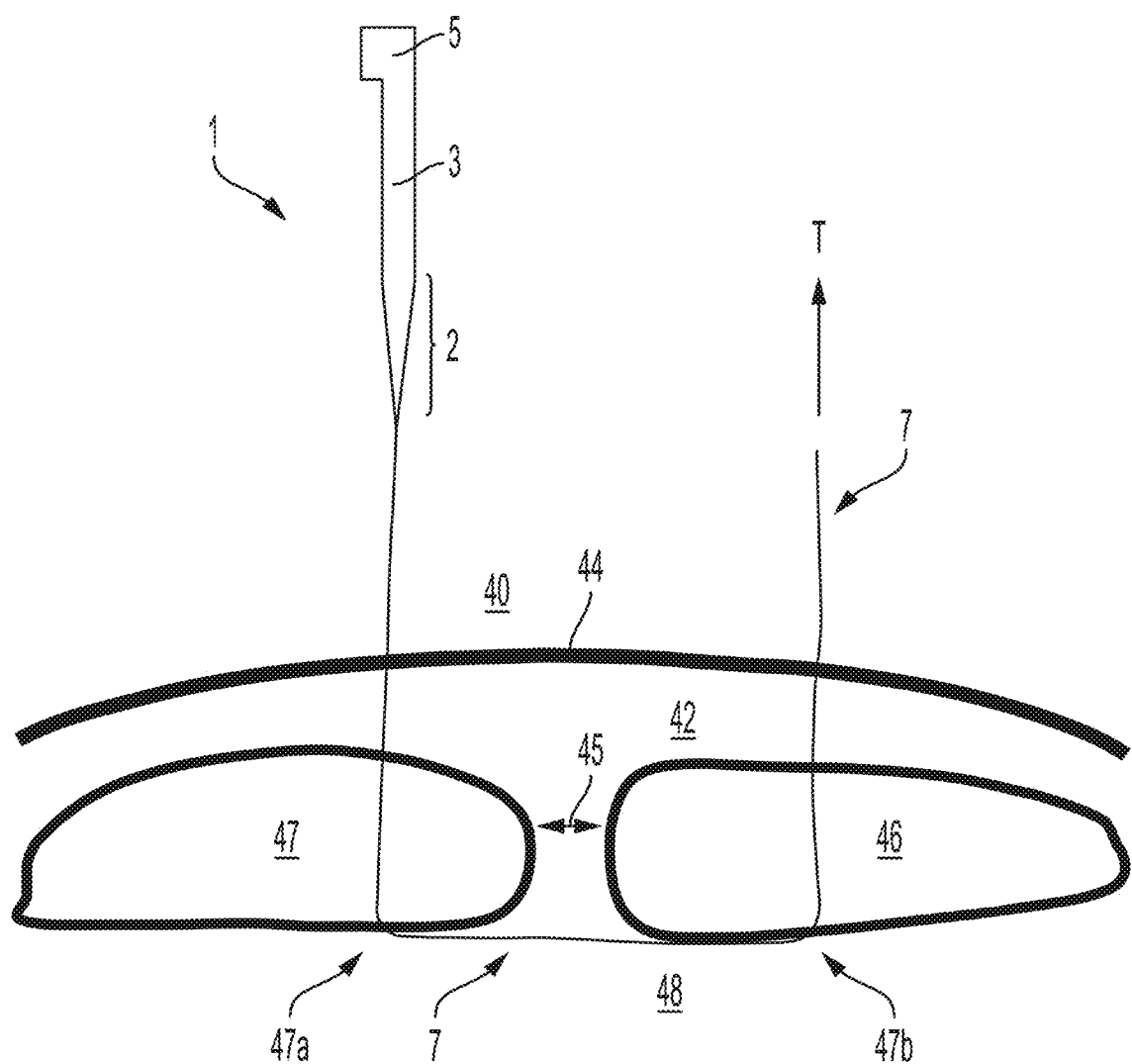
FIG. 9D illustrates steps in an exemplary ventral hernia procedure.

Now with reference to FIG. 9D, which shows another step of a ventral hernia procedure. The leader 7 has been pulled down through the left rectus abdominus muscle 47 and out of the body through the right rectus abdominus muscle 46 in a step aimed at reducing the defect by transiting through the full thickness of the muscle on both sides of the defect, i.e., in contrast to procedures that reduce, for example, the facia. The leader 7 is pulled from the body by the surgeon as indicated by the tension T; the leader is pulled through the full muscle thickness on both sides, and it passes through a first corner 47a and a second corner 47b. Since the leader 7 is small in diameter and highly flexible, it may pass through the holes in the tissue and around the corners with relatively little resistance.

The leader 7 is generally more flexible (less stiff) than the strap 3 due to it having a smaller cross-sectional area and/or by comprising a different geometry or material. In some embodiments, the bending stiffness of the leader may be zero or negligible as it may be a pure tensile member. The leader 7 provides a smaller, more flexible lead-in or pilot through one or more layers of tissue to allow the surgeon to thread the strap into place around a defect. Thus, the leader 7 may be used to guide the strap 3 into place, pulling it through multiple tissue interfaces. In this sense, inserting the device 1 may have a dilating effect in that the smaller diameter leader 7 is pulled through tissue first, leading the larger strap 3 along the same path. Tissue dilation requires a smaller hole and is less traumatic to the tissue. Thus, the leader 7 can be fed through tissue much like a suture (in some embodiments, the leader may be a suture) without significantly affecting the tissue, while the strap 3, once in place, has a larger footprint (width) where it resides within the tissue, thus reducing the pressure applied to the tissue and the risk of cutting into or through the tissue.

An abrupt joint between the leader 7 and the strap 3 may create excessive resistance and may tear tissue or cause the leader to break or the junction between the leader 7 and the strap 3 to break.

Figure 9E:
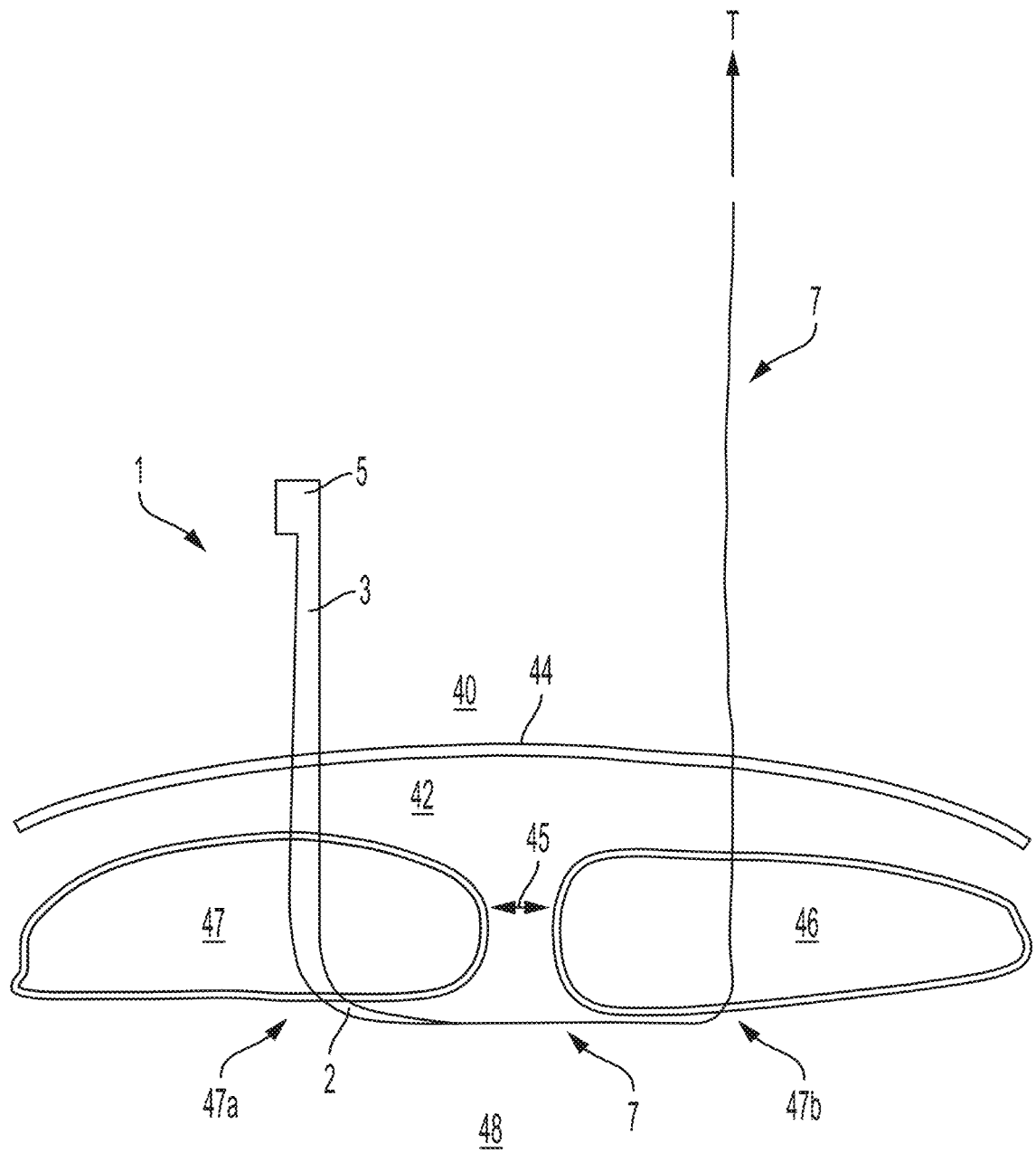
FIG. 9E illustrates steps in an exemplary ventral hernia procedure.

In some embodiments, the device 1 may have a transition section 2 at the distal end of the strap 3 where it joins the proximal end of the leader 7; that is, a section where the leader 7 and strap 3 overlap or are otherwise attached or have a transition in size, shape, or material. The transition section 2 may aid in guiding the strap 3 through the tissue and particularly through corners as it follows the leader 7 by providing a gradual transition in size and/or stiffness between the relatively flaccid leader 7 and the stiffer strap 3. For example, a strap 3 may have a maximum diameter of 2.5 mm while the leader 7 has a diameter of 0.6 mm; the transition section 2 may taper in diameter gradually, but not necessarily monotonically, from the strap 3 size to the leader 7 size over a length to provide a gradual gradient. The length of the transition section 2 may be as small as a 2 mm or for example 5 mm or longer, such as 15 mm or more in some embodiments. For example, FIG. 9E shows another stage of a ventral hernia procedure where the strap 3 is being pulled through a first corner 47a exiting the left rectus abdominus muscle 47 inside of the body cavity 48. The transition section 2 leads the strap 3 through the corner, providing a gradual stiffness transition from the leader 7 to the strap 3, which tends to prevent kinking or excessive resistance, either of which may cause an increase in the tension T required to pull the leader 7.

Figure 9F:
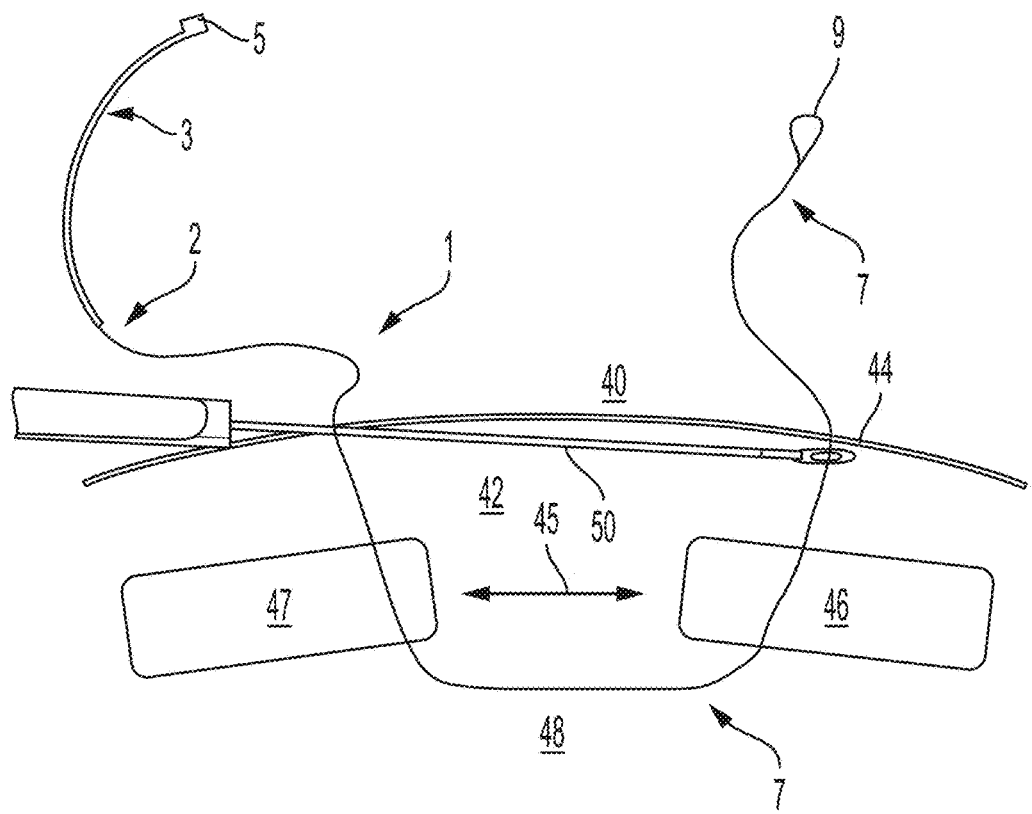
FIG. 9F illustrates steps in an exemplary ventral hernia procedure.
Figure 9G:
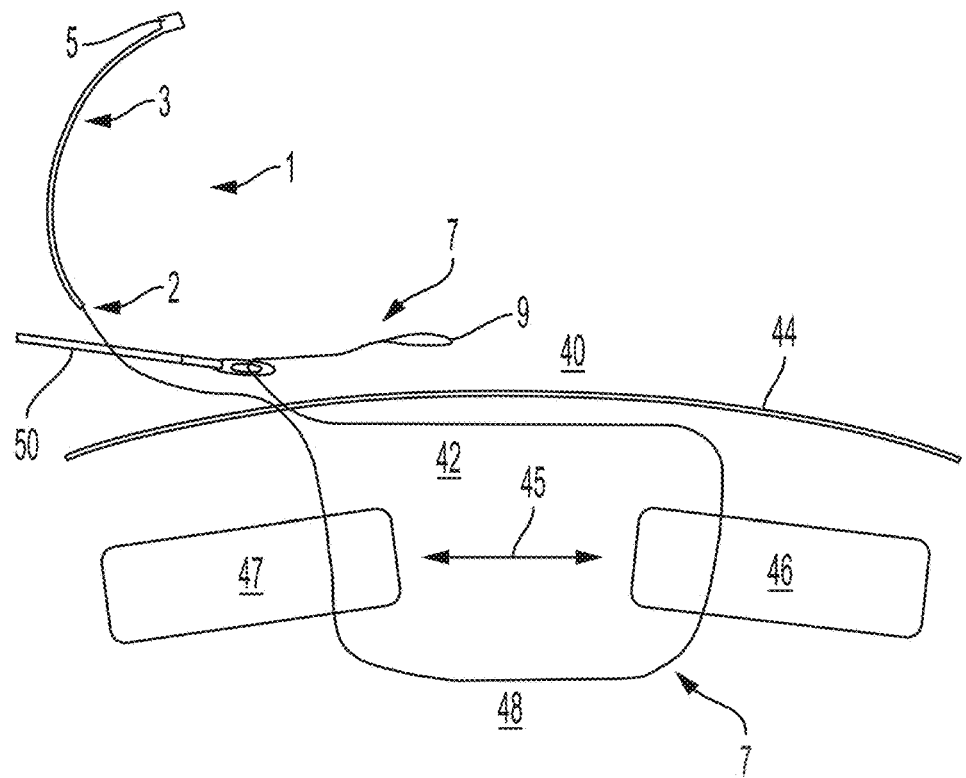
FIG. 9G illustrates steps in an exemplary ventral hernia procedure.
Figure 9H:
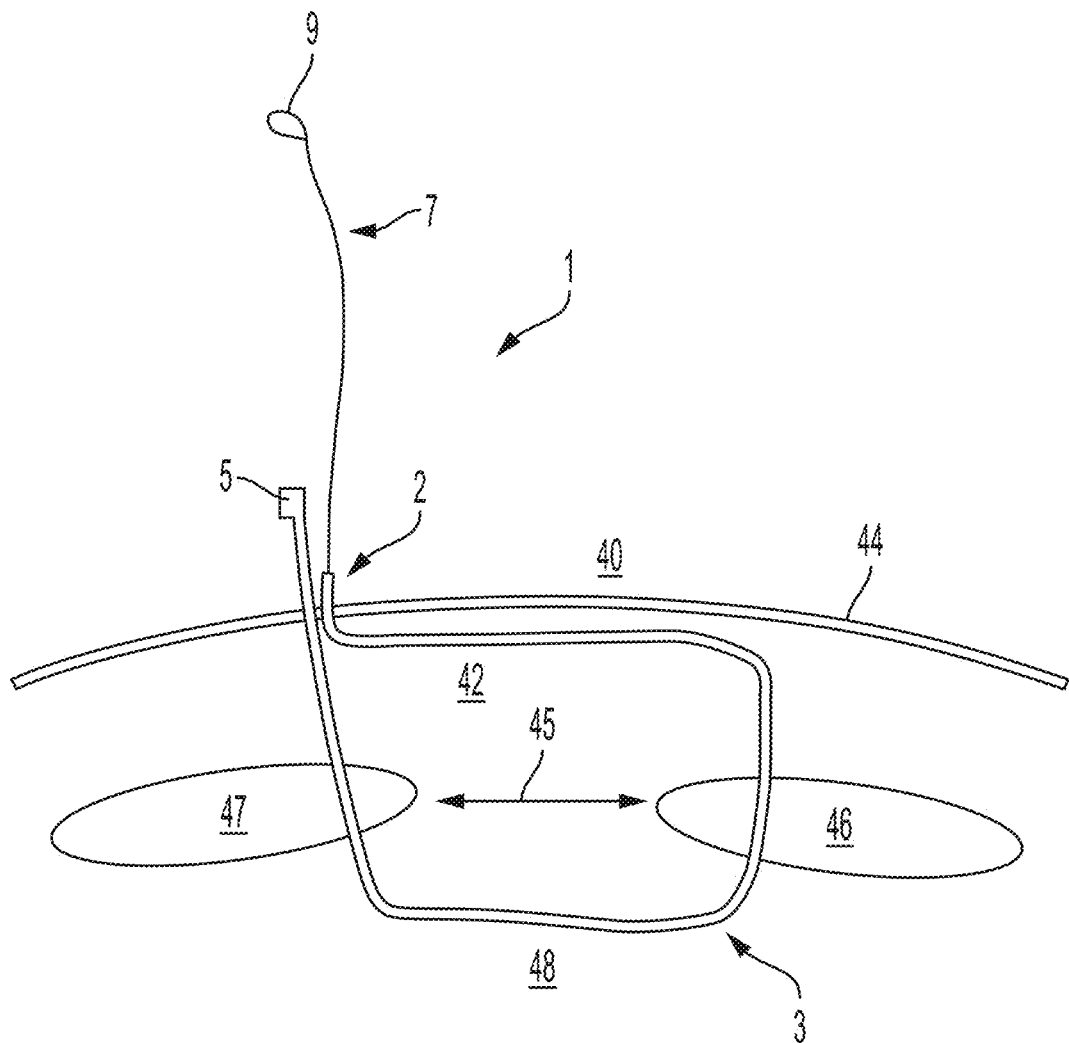
FIG. 9H illustrates steps in an exemplary ventral hernia procedure.
Figure 9I:
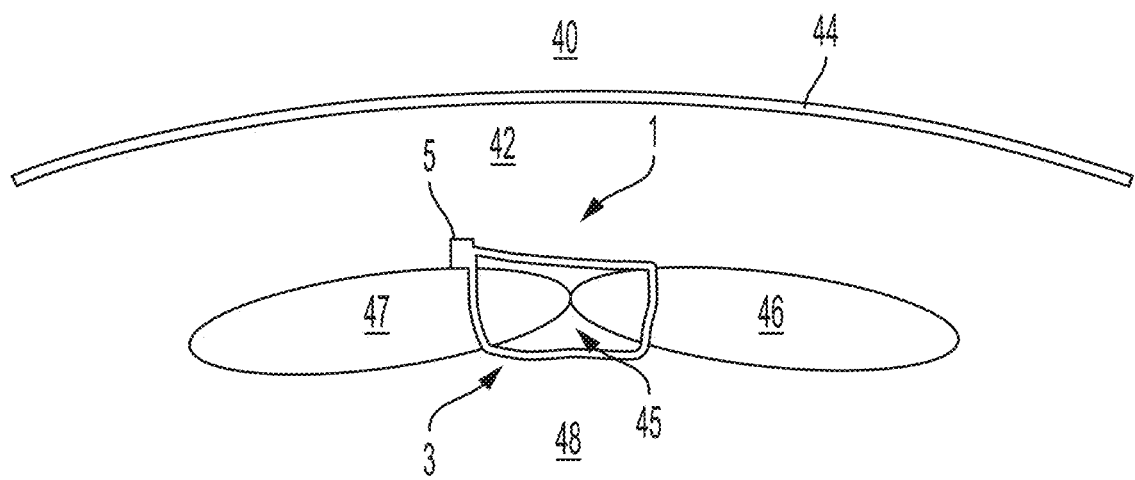
FIG. 9I illustrates steps in an exemplary ventral hernia procedure.

Now with reference to FIGS. 9E-9H, which show another step of an exemplary ventral hernia procedure wherein the distal end of the device is moved across the defect so that the distal end may be joined with proximal end of the device. For example, FIG. 9F shows a crossing guide 50 that is inserted through the first entry hole, where the device 1 is initially inserted, then passed through the subcutaneous region 42 over the defect 45 toward the second hole where the leader 7 has been passed through as shown in FIG. 9E. This allows the crossing guide 50 to engage with the leader 7, as shown in FIG. 9F, so that the leader 7 can be pulled across the subcutaneous region 42, over the defect 45, and out of the body adjacent to the strap 7 as shown in FIG. 9G. One skilled in the art will recognize that there are other ways to move the leader 7 across the subcutaneous region 42. For example, the crossing guide 50 may be placed across the subcutaneous region 42 before the leader 7 exits the body (that is before the step shown in FIG. 9D), such that when the leader 7 is pulled from the body it may be pulled directly through an aperture in the distal end of the crossing guide 50 so that the leader 7 is already engaged with the crossing guide 50 so that the leader 7 can be pulled across the subcutaneous region 42. In other embodiments, the leader 7 may be pushed with a crossing guide 50 or other tool in the opposite direction, that is from the second hole where the leader 7 exits the body to the first hole where the device 1 enters the body. Upon encirclement of the abdominal defect 45 with the leader 7 and advancement of the strap 3 following the leader 7 as in FIG. 9H, the distal end of the strap 3 protrudes through the skin 44 through an incision. It is desirable to align the strap such that the toothed side of the strap 3 faces the inside of the looped strap 3 so that teeth on the strap 3 will properly align with the lock-head 5. In addition, as the skilled artisan will readily understand, it may be desirable to keep any extra length of the strap 3 on the inside of the patient's body, as the leader 7 may easily be entangled and knotted during retrieval of the leader 7 through the lock-head 5 of the strap 3, thus affecting the orientation of the strap 3. As such, the position of the distal end of the strap 3 prior to application of a tensioning and cutting instrument is shown in FIG. 9H. A short length at the distal portion of the strap 3 may extend out of the skin 44, and the toothed side of the distal and proximal sections of the strap 3 face each other. Finally, FIG. 9I shows the device 1 installed in the body as a permanent implant wherein the abdominal muscles 46 and 47 are approximated and the defect is closed. The device 1 has been pulled tightly around the defect 45 and the excess strap 3 beyond the lock-head 5 has been severed leaving little or no excess strap extending beyond the lock-head 5.

Figure 10:
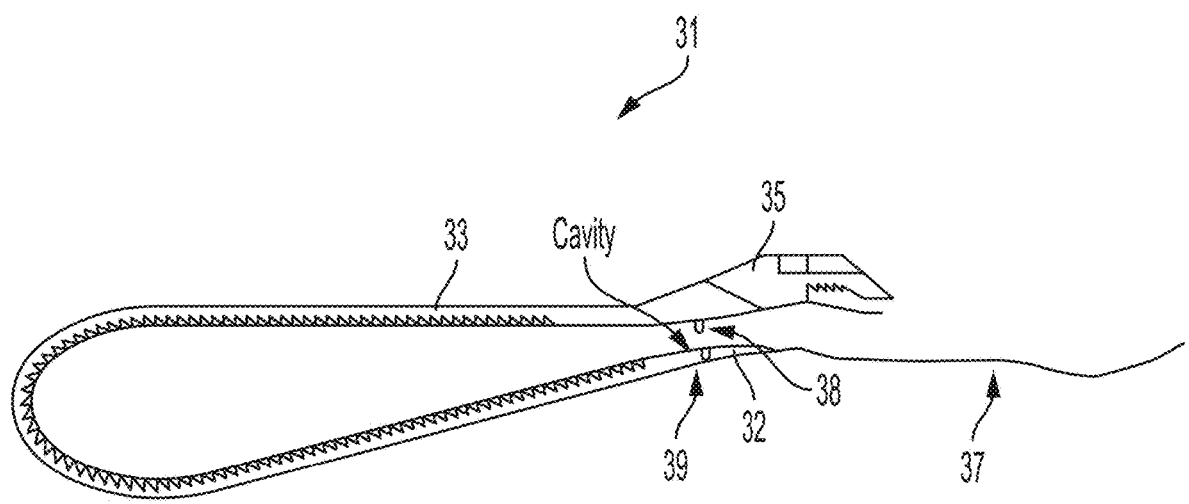
FIG. 10 illustrates a cross-sectional cutaway view of one embodiment of a self-locking strap having a distal strap retaining feature.

In order to ensure that the strap 3 is positioned correctly, a temporary attachment feature may be added to the distal end of the strap and its proximal end, near the lock-head 5; an embodiment of a strap 31 having such a feature is shown in FIG. 10. This temporary locking feature may comprise a post 38 on the strap 31 near the lock-head 35 that has an interference fit with a cavity 39 near the distal end 32 of the strap 31. As the leader 37 is advanced out of the patient until a short length of strap 31 protrudes, the position of the distal end 32 of the strap 31 is temporarily maintained. One skilled in the art would recognize that there are other ways to temporarily lock two members together such as a hook, recess, or a hook-and-loop type of fixation (for example and without limitation, Velcro). These are merely exemplary and, as the skilled artisan will recognize, other methods of temporarily aligning the ends of the strap are within the scope of this disclosure.

Generally, a preferred embodiment of the various devices described herein comprise a configuration wherein the strap is orthogonal to the lock-head.

Figure 11A:
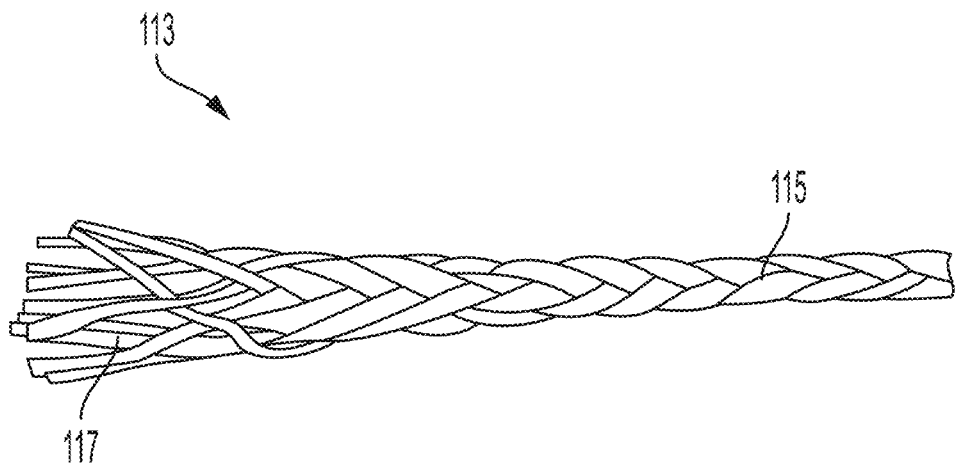
FIG. 11A illustrates a side cutaway view of an embodiment of a mesh leader.
Figure 11B:
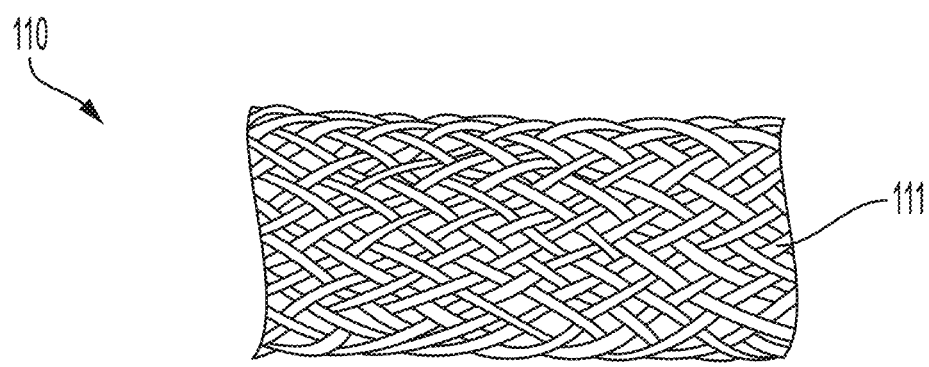
FIG. 11B illustrates a side cutaway view of an embodiment of a mesh leader.

The leader 7 may have a small diameter of less than about 1 mm, though not necessarily round, and should have a very low or negligible bending stiffness and should be able to withstand the tensile forces required to pull a strap through a tortuous path in tissue. As shown in FIGS. 11A-11B, in some embodiments, the leader 110 may be a mesh structure such as a weave, braid, knit, or non-woven fabric sheet. The leader may be tubular in shape, such as a hollow weave, as shown in FIG. 11A, or a flat ribbon, as shown in FIG. 11B. The leader may be extensible such that when it is in tension, it necks down to a smaller size. Furthermore, a leader 113 that is tubular in shape may be flexible enough that it flattens under tension or generally becomes smaller in diameter due to the porosity and layup of the mesh. The leader 113 may have an open end 117 capable of fitting over the distal end of a strap to be secured as further described in this disclosure. In some embodiments the leader may be a tubular braid made of Dacron™, a common thermoplastic polyester (polyethylene terephthalate), having a diameter of approximately 0.7 mm. Alternatively, the leader may be a monofilament, or a suture, that is attached to the strap, and it may be an integral molded extension of the strap that is smaller in cross-sectional area so as to be easier to thread through tissue.

The leader portion may be made of a different material from the strap, or it may be made of the same material, but in a different geometric configuration such as a mesh or a solid structure having a different cross-sectional shape than the strap. For example, the leader can be a wire or strip made from a metal such as stainless steel or nitinol. It should be appreciated, however, that the leader can be made from other materials, such as Polyether ether ketone (PEEK) or polyethylene, or for example, a suture material, as described further below in the materials section. The leader can have any length as desired, depending on the anatomy and surgical technique. For example, the leader may be relatively long enough to reach through tortuous paths in a ventral hernia surgical procedure as described below, especially with an obese patient, which may require a relatively long leader and strap. While a length of greater than or equal to about 50 cm for the entire device may be appropriate for some patients, the device may need to be greater than or equal to about 1200 cm, or as much as greater than or equal to about 2400 cm long for some patients. The leader length may be a fraction of the length of the device, for example, 50%, such that the leader and strap are approximately the same lengths, or for example, the leader may be as much as 75% of the length of the device or as small as about 25% of the length of the device. The length of the leader may be chosen so that the leader is easy to grasp and control while pulling the strap through various layers of tissue. As the leader will be severed after the strap is in place, any excess length is merely discarded; however, it may be cumbersome if the leader is excessively long as it may interfere with the surgery or it may add excessive material or manufacturing (component or tooling) costs. Similarly, the strap will eventually be severed to leave only a small portion of the distal end outside the lock-head, that is after fully approximating tissue.

Some or all of the length of the leader may have a size of approximately 0.35 mm up to approximately 2 mm in its major cross-sectional dimension or even greater in some applications. Therefore, the entire length or at least a majority of the length of the leader can have a cross-sectional area that is between about 0.3 mm$^2$ and about 13 mm$^2$. It should be appreciated, however, that the leader can have cross-sectional areas such that the ratio falls outside of the stated range. For example, the leader may be a small wire or suture having a diameter of between 0.1 mm and 0.35 mm.

The proximal end of the leader 7 may be coupled to the distal end of the strap 3 either after or during the molding of the strap 3, for example as an overmold or insert mold, or the entire device may be molded as one part. The proximal end of the leader 7 may be overmolded onto the distal end of the strap 3 when the strap 3 is being formed via injection molding; in these embodiments, the leader 7 may be the same material as the strap 3, and the device 1 may be made as a single, contiguous part with an integral lock-head. Alternatively, the distal end of the strap 3 can include a metal insert, and the proximal end of the leader 7 can be coupled to the metal insert. It should be appreciated, however, that the leader 7 can be coupled to the strap 3 by other connections, for example, by a knot tied around the strap 3 or looped through a hole in the strap 3 and tied. Regardless of the structural and geometric nature of the transition section 2, the cross-sectional size of the transition section 2 should be comparable in size or smaller than the strap 3 so as to pass through layers of tissue minimizing resistance and tissue tearing. While the device may be cut at any location during the procedure to remove the leader and any excess strap, in some embodiments, the transition section 2 may be detachable. That is, it may have a relief, cutout, inserted/captive joint, or similar feature that makes it weaker in strength as compared to the remainder of the device such that it may be pulled apart by hand; that is, the leader 7 may be separated from the strap 3 by pulling on it with a force in excess of the force required to pull the strap through the body so that it will not inadvertently separate, but lower than the force that will break the strap. For example, if it takes lb of tensile force to pull the leader and strap through the body and the tensile strength of the strap is 7.5 lb, then a break-away force of between about 1 lb-7.5 lb is desired. In some embodiments, the leader may also be quick released by the operator twisting or tearing to separate it from the strap.

Figure 12A:
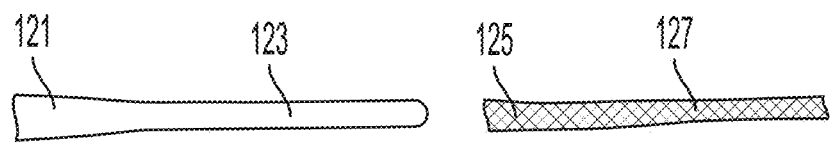
FIG. 12A illustrates a top cutaway view of an embodiment of a method for attaching a leader to a strap.

In embodiments where the leader 7 is of a tubular shape or made of a mesh or other porous structure, pulling it in tension may tend to decrease its diameter. In such designs, the leader may grip onto the strap 3 in the transition section, forming a low-profile joint. The strap 121 may have a reduced diameter at its distal end in the transition section 123 to accommodate a relatively smaller leader 127, as shown in FIG. 12A which shows the proximal end 125 of the leader 127 before sliding it over the transition section 123 during manufacturing. The transition section 123 may have features such as one or more larger diameter bulges to hold the leader 127 in place when the leader is not in tension, such as during manufacturing; however, when it is pulled in tension, for example, when threading it through tissue, it will tend to decrease in diameter, thus gripping onto the transition section of the strap. The leader 127 may be tapered or have a reduced cross-sectional dimension in the transition section 123 to match that of the distal end of the strap 121. Alternatively, the leader 127 may be larger in diameter, or stretched to be larger in diameter, in the transition section 123 if the leader 127 is of a smaller diameter or cross-sectional dimension than the strap 121. For strap designs, such as that shown in FIG. 12A having a non-circular shape, "diameter" refers to the largest cross-sectional dimension.

Figure 12B:
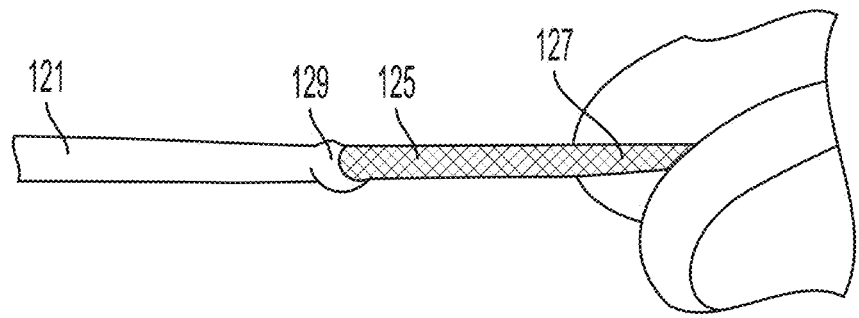
FIG. 12B illustrates a top cutaway view of an embodiment of a method for attaching a leader to a strap.

FIG. 12B shows leader 127 advanced onto the strap 121 with a small amount of adhesive 129 added to the proximal end 125 of the leader 127 to tack the leader 127 to the strap 121. The adhesive 129 provides an end constraint such that when the leader 127 is pulled in tension and held by the adhesive bond, the leader 127 reduces or necks-down in diameter and clamps onto the strap 121 (FIG. 12B). Thus, the adhesive 129 acts in concert with the tightening action to create a strong joint between the leader 127 and the strap 121 that increases in strength with tension. The joint may be further strengthened by adding an adhesive layer substantially covering the entire transition section 123 where the leader 127 overlaps and grips the strap 121.

Additionally or alternatively, a heat shrink fitting may be placed over the strap and leader to further reinforce the joint such that, when heated, the heat shrink element bears down on the transition section and holds the leader onto the strap in the transition section. In other embodiments, the leader may be simply bonded to the strap, and the strap may be narrowed in the transition section so as not to increase the thickness. Similarly, if the leader is a strip of material, rather than a tubular structure, it may be bonded to one side of the strap or heat staked (thermally bonded) or ultrasonically welded onto the strap.

Any combination of the approaches disclosed herein or known to those skilled in the art for coupling two elongate members may be employed. In some embodiments, a crimp may be placed around both the leader and the strap such that it can be deformed to hold the two components together. Furthermore, in some embodiments, the mesh may be woven through or around the strap, or the leader may be looped and tied to the strap.

As yet another example, the leader may be an off-the-shelf suture that is tied onto the end of the strap through a feature such as a hole, notch, shoulder, or other feature for receiving the suture. Similarly, the leader may be a metal wire or 2D strip having low bending stiffness so that it may be manipulated in relatively tight spaces within the body. The wire or strip may be overmolded with the strap or otherwise attached to the strap using methods described herein or other methods known to one skilled in the art.

Figure 13A:
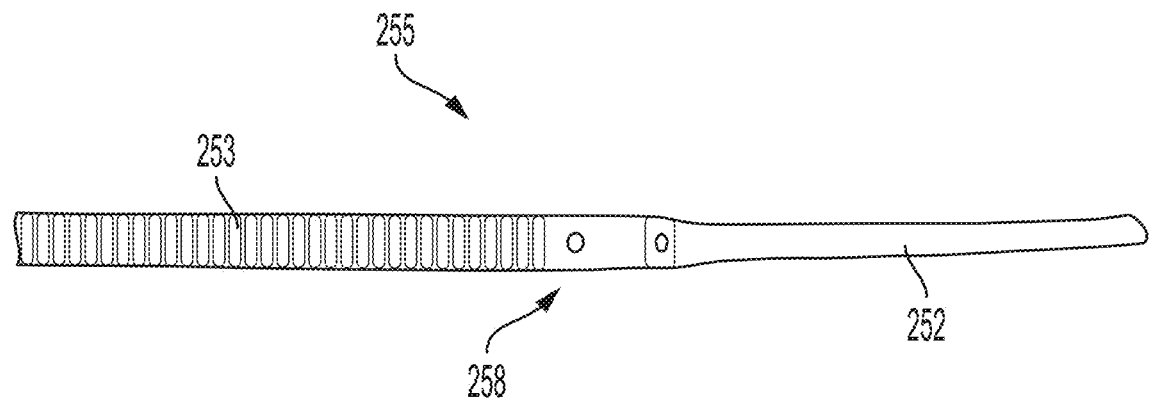
FIG. 13A illustrates a cutaway view of an embodiment of a method for attaching a leader to a strap.
Figure 13B:
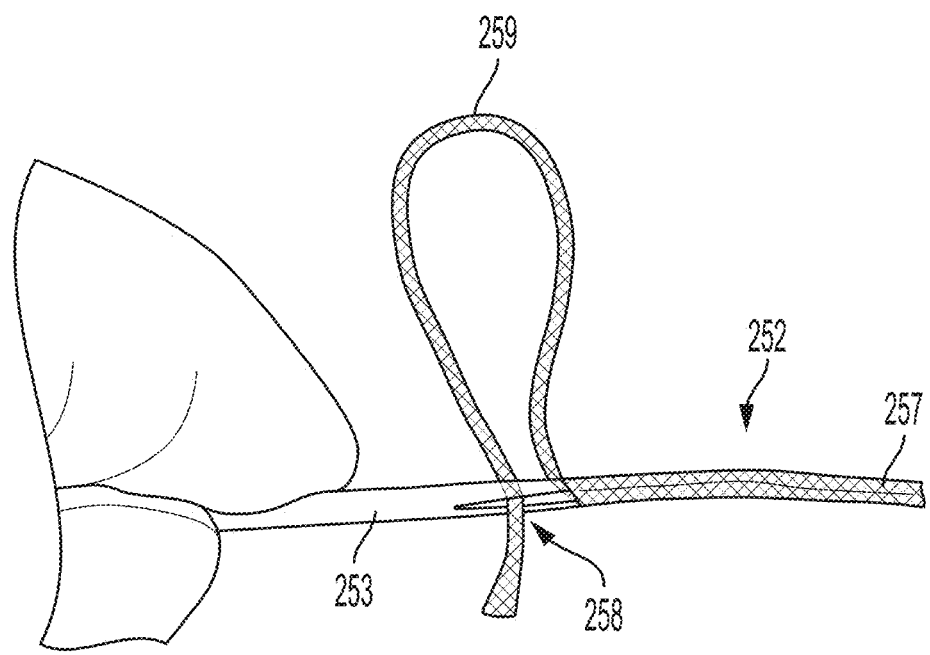
FIG. 13B illustrates a cutaway view of an embodiment of a method for attaching a leader to a strap.
Figure 13C:
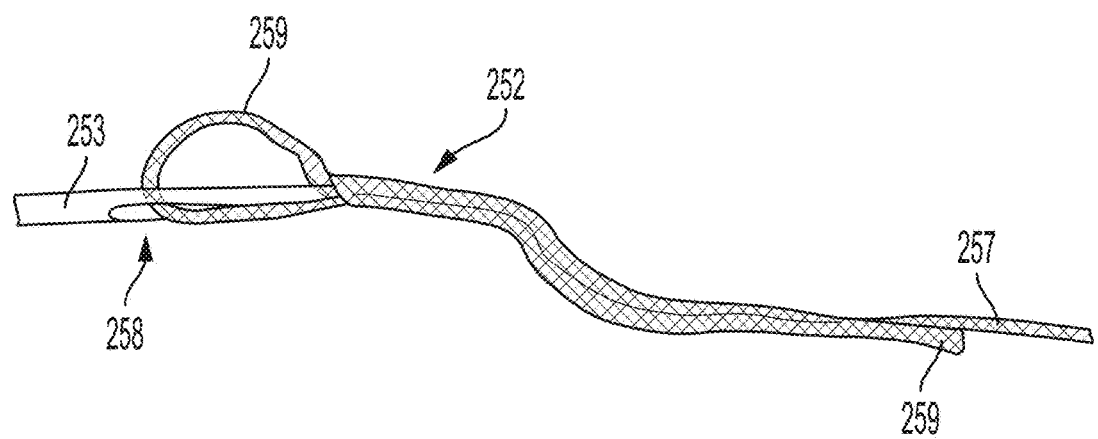
FIG. 13C illustrates a cutaway view of an embodiment of a method for attaching a leader to a strap.
Figure 13D:
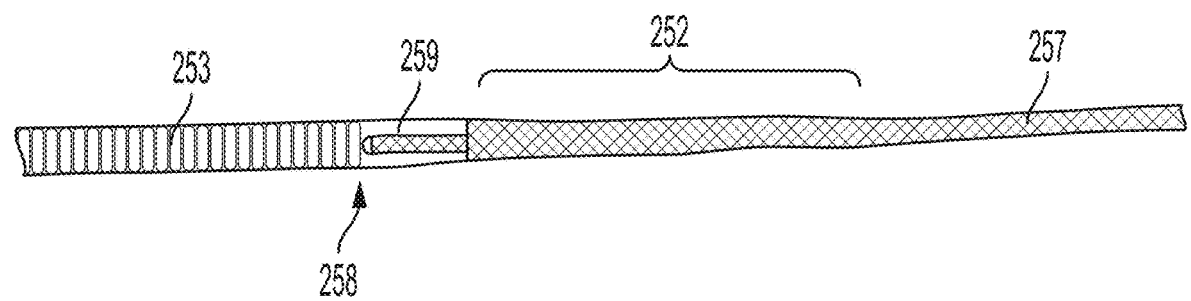
FIG. 13D illustrates a cutaway view of an embodiment of a method for attaching a leader to a strap.

As noted above and shown in FIG. 12B, in some embodiments, when a tubular leader is retrained from translating off of the end of the strap, the leader tends to collapse radially when pulled, much like a finger trap, gripping the strap and thus increasing the strength of the joint as it is pulled. While the embodiment in FIG. 12B uses an adhesive to restrain (or tack) the end of the leader, FIGS. 13A-13D illustrate another means of restraining the leader by looping through a hole in the strap. The device 255 shown in FIG. 13A has a hole 258 through a portion near the distal end of the strap 253 that is located on or near the transition section 252, where the strap 253 has a reduced size. A portion of the proximal end 259 of the leader 257 is fed through the hole 258, as shown in FIGS. 13B and 13C and then fed through the lumen of the leader 257 so that the proximal end 259 resides inside of the leader 257; excess length of the proximal end 259 of the leader may be pulled out of the side of the leader 257 and cut off. FIG. 13D illustrates the final configuration after the leader 257 is pulled tight away from the hole 258 causing it to squeeze down on the strap 253 in the transition section 252 resulting in a smooth, tapered section having a size and stiffness gradient from the stiffer strap 253 toward the leader 257 which may have negligible bending stiffness.

In other embodiments, the leader may be made as a contiguous component with the strap; that is, the leader, strap, and even the lock-head may be molded as one component such that the leader may have a shape that provides a lower bending stiffness than the strap. For example, the device may be extruded or molded with a variable shaped cross-section such that the cross-sectional shape of the strap differs from that of the leader. Alternatively, the leader may be attached to the strap after both parts are made; such applicable joining techniques include but are not limited to bonding, ultrasonic welding, heat staking (thermal bonding), or in the case of metals, welding, or crimping. Still more alternatively, the leader may be a mesh or fabric that is overmolded (or otherwise combined) with soft plastic or elastomer. The overmold section remains flexible and provides the surface area to distribute the load over tissue mitigating the cheese wire effect of suture. The continuous integrated leader provides the tensile strength necessary to maintain closure of the tissue defect.

The device may have a color that contrasts with the tissue in the body cavity as seen through a laparoscopic camera or using colors not typically seen in the human body so that the surgeon may easily identify the device in tissue or within the body cavity. For example, the device may be a yellow, blue, green, or orange or bright or fluorescent tones of each. Furthermore, the leader or the loop (or other protuberance) may be colored differently from the strap so that the leader can be identified within the body easily since the surgeon may initially need to see the leader to manipulate the device. In one embodiment, the permanently implantable strap may be of a natural molded plastic color, that is, with little or no coloring dye to enhance long-term biocompatibility; such plastics may appear white, or somewhat translucent, or off-white to yellow, for example, for a strap comprising PEEK. The leader may be blue or orange, so that it contrasts with both the strap and the tissues in the body.

In some embodiments, it may be desirable to visualize the device or certain parts of the device, such as the leader, loop, lock-head, or strap via x-ray (or fluoroscopy) inside the body. One or more of these sections may be made of a radiopaque material such as a metal like stainless steel or nitinol, or a plastic with a radiopaque die or blend of radiopaque materials such as barium sulfate, bismuth compounds, or metals such as tungsten or steel. One skilled in the art would recognize that there are many compounds and formulations that result in a radiopaque polymer.

In some embodiments, the loop may have or define an overlap section where the leader is joined to itself at, or proximate to, the proximal end of the loop. The overlap section may have slightly higher stiffness than the rest of the leader due to the doubling of materials and to any added glue or crimp elements; this gives the loop more resistance to deforming when it is dwelling in the body. That is, the added stiffness provides resistance to prevent the loop from moving away when it is contacted by a tool, such as a suture grasper or snare. This may facilitate easier grasping because the loop will be less likely to fall away from a tool as it engages with the loop. One skilled in the art would recognize that there are many features that can be located at or near the distal tip of the leader that can enable grasping, such as one or more protuberances such as a ball, or a notch, a zig-zagged tip, or a "J" shaped tip. Such embodiments provide a feature that may be easily grasped while still having a small size that is capable of passing through a small skin incision or a small hole in tissue.

Figure 14:
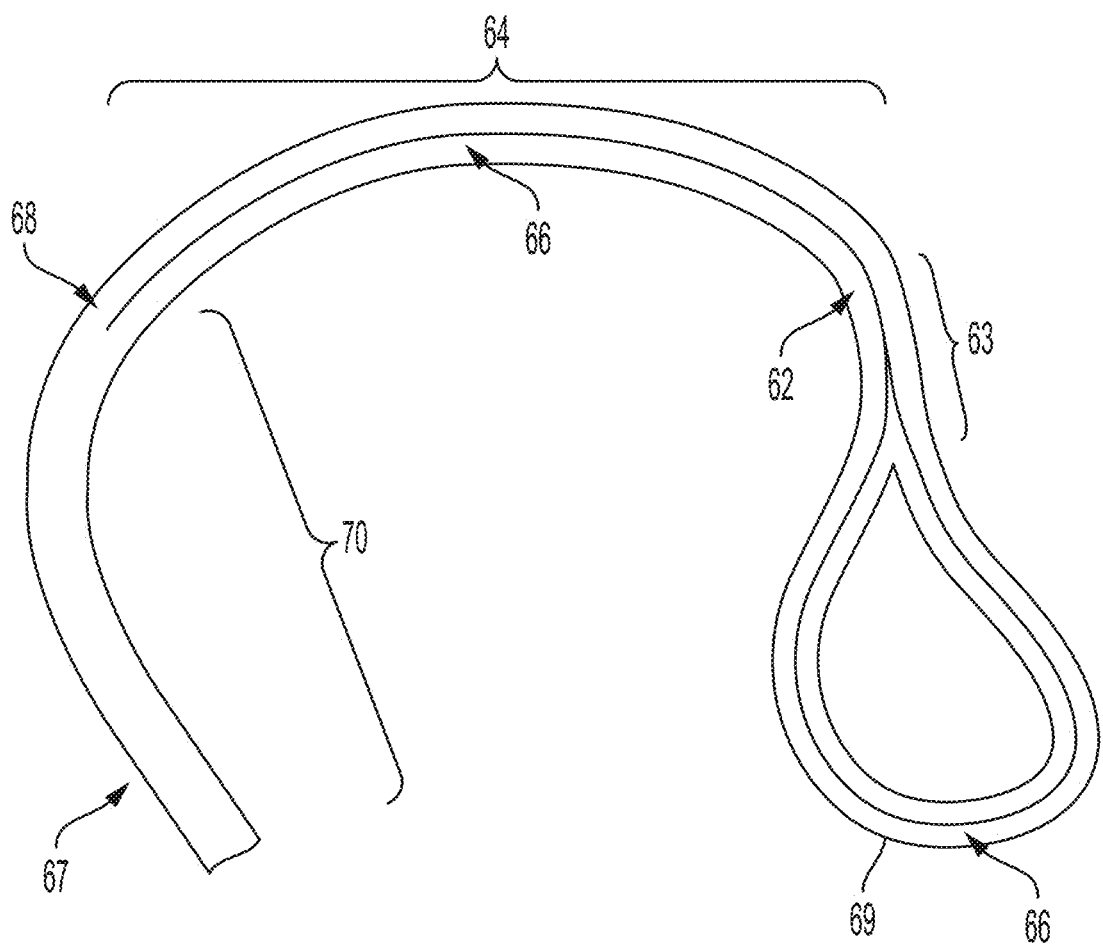
FIG. 14 illustrates a top cross sectional view of an embodiment of a leader having stiffening zones.

In some leader embodiments having a tubular shape, the loop may derive added stiffness form a monofilament core through the lumen of the loop. Additionally, the monofilament may extend back down into the leader to provide a tiered stiffness along the leader. With reference now to FIG. 14, the distal end of a leader 67 is shown having a loop 69 and a stiffening element 66 inside of the lumen and around the loop 69. The stiffening element 66 may be a monofilament made of a polymeric material such as polypropylene, Nylon or polyethylene, for example. However, one skilled in the art would recognize that there are many flexible, narrow filaments that can be used to stiffen the distal end of the leader 67. The stiffening element 66 starts at a first end 68 located proximal to the loop 69, and passes around the loop 69, where the second end 62 resides just proximal to the loop 69. This arrangement results in several regions along the leader 67 having different stiffnesses. The bulk of the leader 67, as designated by zone 70, has no stiffening element and, as such, has the baseline flexibility of the unaltered leader. Zone 64 has one stiffening element 66 through the lumen and, as such, has more stiffness than zone 70. Zone 63 has an even larger stiffness due to the overlap of the stiffening element 66 in the relatively short zone 63. The loop 69 has a stiffness similar to that of zone 64 because it has a single stiffening element 66 through the lumen. The stiffness gradations along the leader 67 can be tailored to produce a desired effect or behavior when the leader is inside the body. In some embodiments, the added stiffness may make the distal leader less flaccid, such that it will tend to resist sticking to tissue inside the wet environment of the body cavity. The stiffness may also make the loop 69 easier to grasp because it will tend to have more reaction force to any surgical grasper incident upon it; that is, it will tend to not simply move away when pushed.

In some embodiments, the stiffest section, zone 63, may have a length ranging from about 5 mm to about 80 mm and zone 64 may be approximately 50 mm to about 200 mm in length. In one embodiment zone 63 is about 50 mm long and zone 64 is about 100 mm in length.

As described elsewhere herein, the stiffening zones 63 and 64 and loop 69 may comprise a shape memory material, e.g., a shape memory metal, shape memory alloy such as Nitinol and/or a shape memory polymer, adapted to maintain desired undeformed shapes. In the case of the loop 69, the shape memory material may be adapted to hold the loop 69 in an opened configuration by using the superelastic (or pseudosuperelastic) properties to generate the desired undeformed shapes as the skilled artisan will now readily understand in the subject context.

Figure 15:
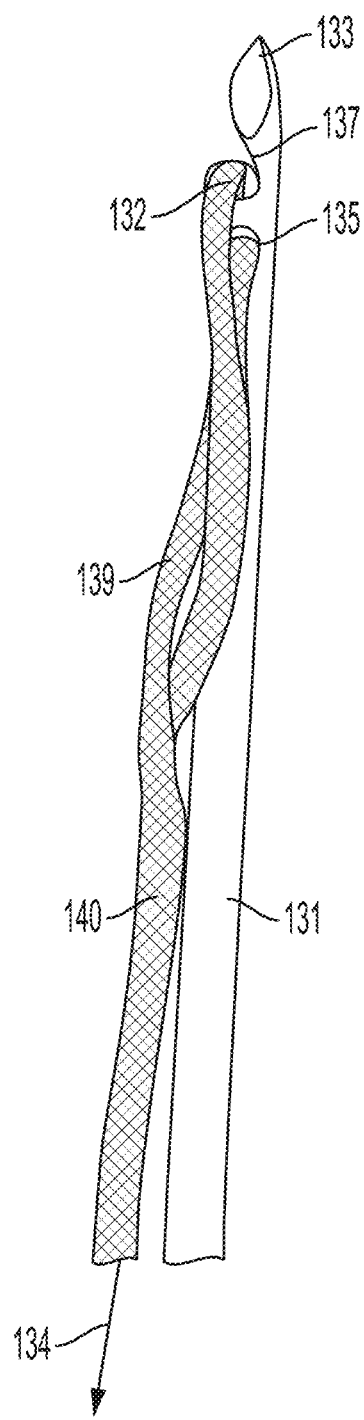
FIG. 15 illustrates a side cutaway view of an embodiment of a distal loop attached to a suture passer.

In addition to providing a grasping feature for accessing the leader from within the body, the loop may also facilitate insertion of the leader through tissue. FIG. 15 shows a leader 140 having a loop 139 that is mounted on a suture passer 131. The suture passer 131 has a beveled tip 133 for piercing tissue and a cutout 137 (or hook) to hold the loop 139. In operation, the leader 140 may be pulled in tension along the length of the suture passer 131 as indicated by arrow 134 so as to pull the loop tip 132 against the cutout 137, so that the loop 139 stays on the suture passer 131 as it is driven through layers of tissue. In other embodiments, a suture passer may have a hook or clasp mechanism near the tip to hold the loop securely; in such case, the leader may not need to be held in tension because the loop will be captive. The suture passer 131 may have a second cutout 135 to catch the loop 139 from within the body to pull the leader 140 out from the body.

Figure 16:
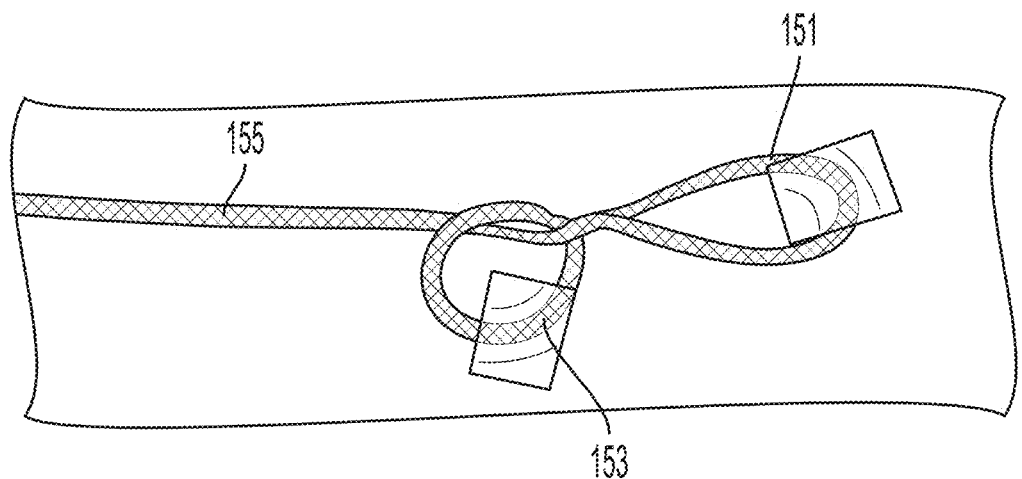
FIG. 16 illustrates a side cutaway view of an embodiment of a double loop at the distal end of a leader.

Now with reference to FIG. 16, an embodiment of a leader having two loops is shown; the leader 155 has a distal loop 151 and a proximal loop 153. The distal loop 151 may be used as described above, that is, to pull the leader 155 into the body via a suture passer (not shown, but see FIG. 16). Once the distal loop 151 is in the body cavity, the distal loop 151 may be retained by the suture passer so that the leader 155 is held in place without wandering, then the proximal loop 153 is held steady while a surgical grasper or other grasping tool is used to grab onto the proximal loop 153. This handoff may be performed inside the body blindly, that is, by feel, or more commonly under visualization with a laparoscope. Furthermore, the leader design having two loops may obviate the need for a laparoscopic grasper, hence removing the need for another incision site. This is because the suture passer used to introduce the leader into the body cavity may stay engaged with one of the loops, for example, the distal loop 151, while dwelling inside the body. With the leader captive, another suture passer or similar device can be introduced through a second incision, and both devices can be angled together such that the second suture passer can grasp the proximal loop 153.

Figure 8:
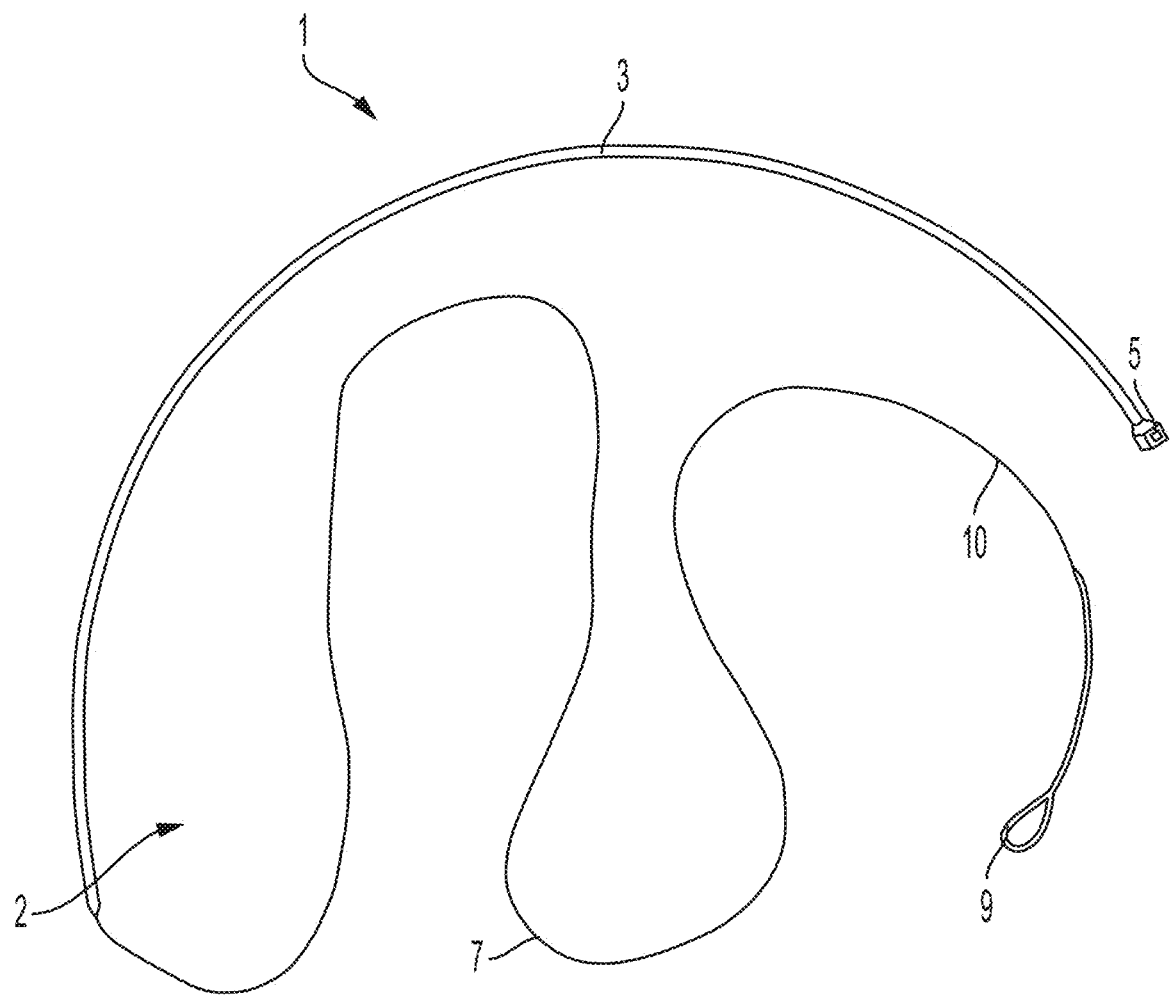
FIG. 8 illustrates an embodiment of a self-locking strap embodiment.
Figure 17:
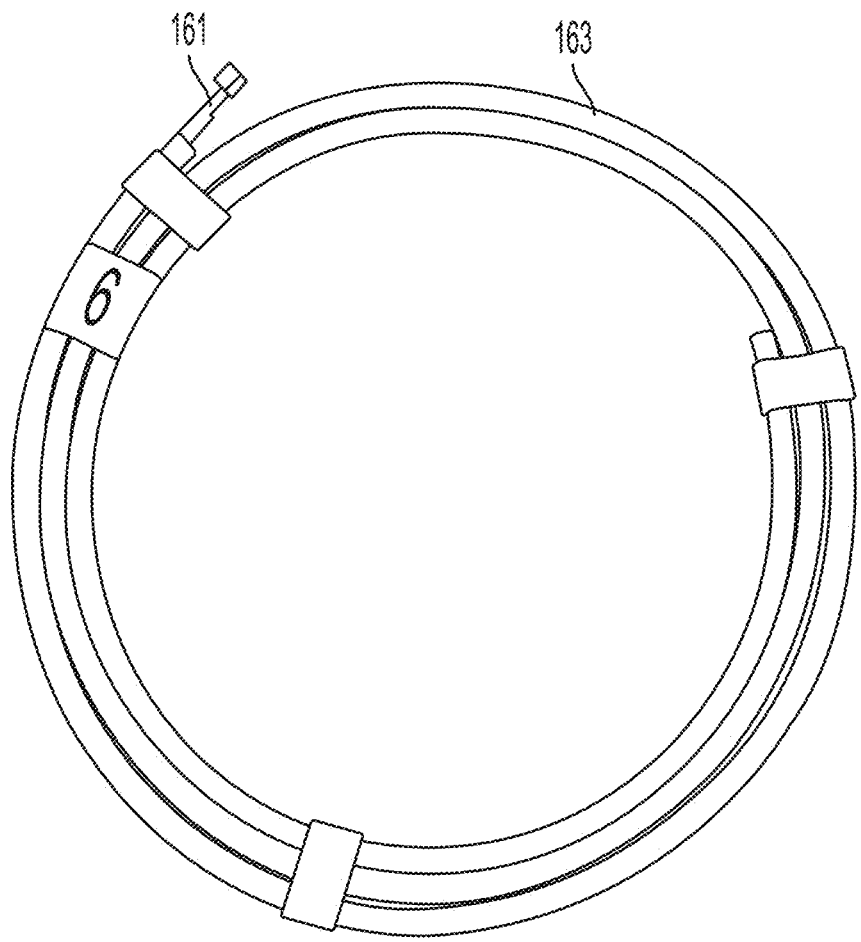
FIG. 17 illustrates a top view of an embodiment of a strap packaged in a wound tube.

The device (strap and/or leader and/or transitions section) may be pre-curved so that when the surgeon removes the device from the package, it has some curvature in all or part of the structure; e.g., see FIG. 8 wherein the strap 3 is curved. In the most preferred embodiments, leader is flaccid, i.e., without appreciable bending stiffness, but some embodiments may comprise a pre-curved section which may provide a small amount of bending stiffness in that pre-curved section. The pre-curved section on strap 3 primarily ensures that the strap teeth are on the inner diameter of the loop and, secondarily, allows the device to follow a natural path when inserted into the body cavity across the wound defect to be treated. The curvature may be small (e.g., a 3" radius) or large (e.g., a 10" radius), or any radius in between because any curvature will tend to bias the device in the direction toward the opposite side of the wound to facilitate easier grasping, manipulation, and threading through the incisions. However, a device with too much curvature may provide too much resistance when passing through tissue. The device may be molded in a curved shape, or it may be packaged in such a way that the material takes a set, for example due to the material exhibiting creep while in the package. FIG. 17 shows an embodiment of such a package wherein the device 161 is placed through a tube 163 that is wound in a circle. In addition to this tubing package, there are many arrangements within the scope of the present inventions to package the device in a curved configuration such as restraining the device in a cardboard cutout package or placing the device into a thermoformed plastic tray that is shaped in such a way that all or part of the device is curved. Alternatively, a shape memory or superelastic material such as, without limitation, Nitinol may be employed to achieve the undeformed pre-curved or prebent shape.

Figure 18A:
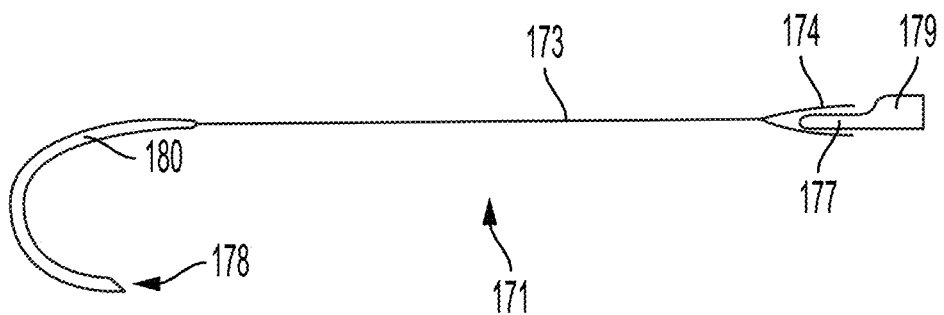
FIG. 18A illustrates a side view of an embodiment of a mesh strap with an attached needle and lock-head.

In other embodiments, the strap section (the permanent implant) of the device may be a mesh structure similar to the leader embodiments described above and shown in FIG. 12A for example. The strap may be comprised of a weave, braid, knit, or nonwoven sheet, that may be tubular in shape or having a flat 2D shape like a ribbon or other mesh-like structures. FIG. 18A shows a side view of such a device 171; the strap 173, is a mesh structure having a tubular form or a flat cross-section, both of which tend to lay flat onto tissue and form a contact area that is generally larger than that of a suture thus providing less pressure on the tissue, reducing the tendency to cut into the tissue. The device 171 may have a needle 180 at its distal end and a bevel 178 at the tip of the needle for puncturing tissue. The needle 180 may be straight or curved, as shown, to facilitate suturing a tissue defect such as a ventral hernia. Alternatively, the device 171 may not have a needle at the distal end but instead may have nothing, a narrowed distal tip, a leader, or one or more loops as disclosed described above in the various leader embodiments.

Figure 18B:
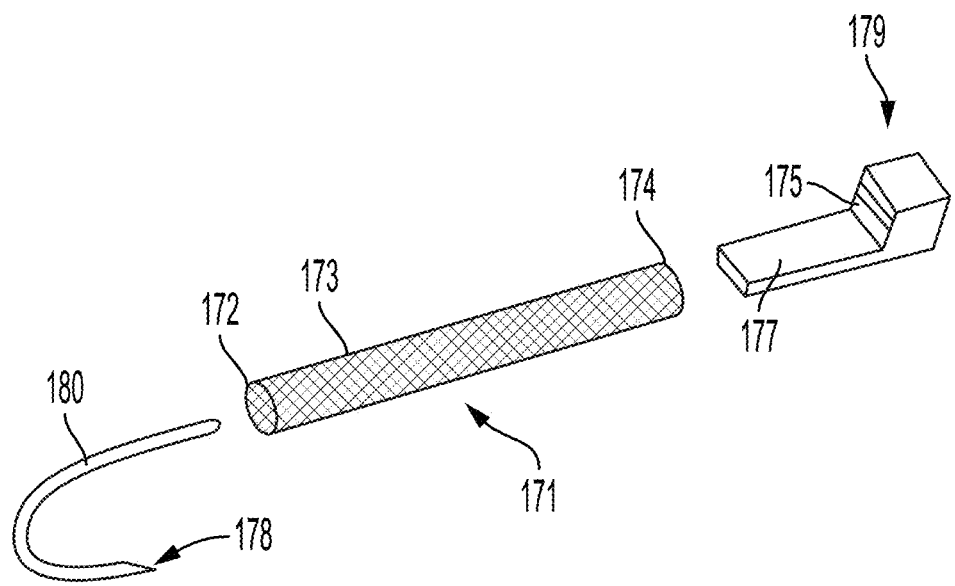
FIG. 18B illustrates a side exploded view of an embodiment of the mesh strap with needle and lock-head of FIG. 19A.

The proximal end of the device 171 may have a lock-head 179 that only allows one-way motion of the strap 173 as it passes through the lock-head 179. The strap 173 may be attached to the lock-head 179 in the same manner as described in this disclosure for connecting the strap 3 to the leader 7 (e.g., see FIGS. 12A-B and 13A-D). For example, as shown in FIGS. 18A and 18B, the strap 173 may have an opening at its proximal end 174 that envelops a tab 177 extending from the lock-head 179. The tab 177 may be similar to the transition section 123 shown in FIGS. 12A-B and 13A-D, and it may have a tapered profile or a straight profile, and it may also have one or more bumps or bulges over which the strap 173 passes. FIG. 18B shows an isometric, exploded view of the device 171, comprising a strap 173 that is a flexible mesh structure having an open lumen therethrough, or at least partially therethough and a distal end 172. The lock-head 179 has an aperture 175 that is capable of receiving the strap 173 restricting the movement of the strap 173 in one direction.

Figure 18C:
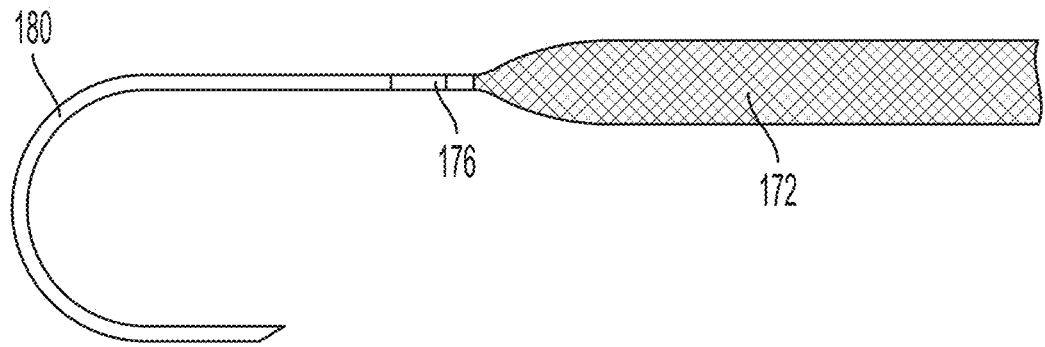
FIG. 18C illustrates a side cutaway view of an embodiment of a mesh strap with an attached needle and lock-head.
Figure 18D:
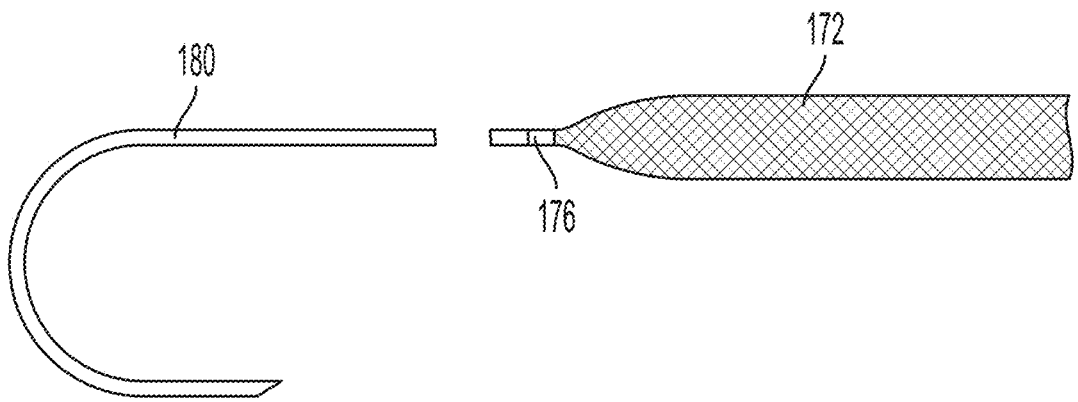
FIG. 18D illustrates a side exploded cutaway view of an embodiment of the mesh strap with needle and lock-head of FIG. 19C.

In some embodiments, the needle 180 may be left on the strap 173 such that the needle 180 guides the strap 173 into the lock-head 179, after which the needle 180 may be cut from the strap 173. In other methods, the needle 180 may be cut from the strap 173 before threading through the lock-head 179. Depending on the layup of the mesh, the distal end of the strap 173 may fray where it is cut, making it difficult to thread through most types of lock-heads—at least those having an aperture. The distal end 172 of the strap 173 may have a leader section 176 at its distal end near the needle 180 as illustrated in FIGS. 18C-18D. As shown in FIG. 18C, the distal end 172 of strap 173 has a leader 176 having a smaller cross-sectional shape near the attachment to the needle 180. The leader 176 may be a section with a tighter weave and smaller diameter, or it may be bonded or otherwise formed into a smaller shape or melted to a smaller size and so that the fibers are not loose or do not come loose after it is severed. Due to these manufacturing treatments, the leader 176 may be stiffer than the strap 173, or remainder of the strap 173, so that it is easier to push through a lock-head without folding over or buckling, as it may have more column strength than the strap 173.

Figure 19A:
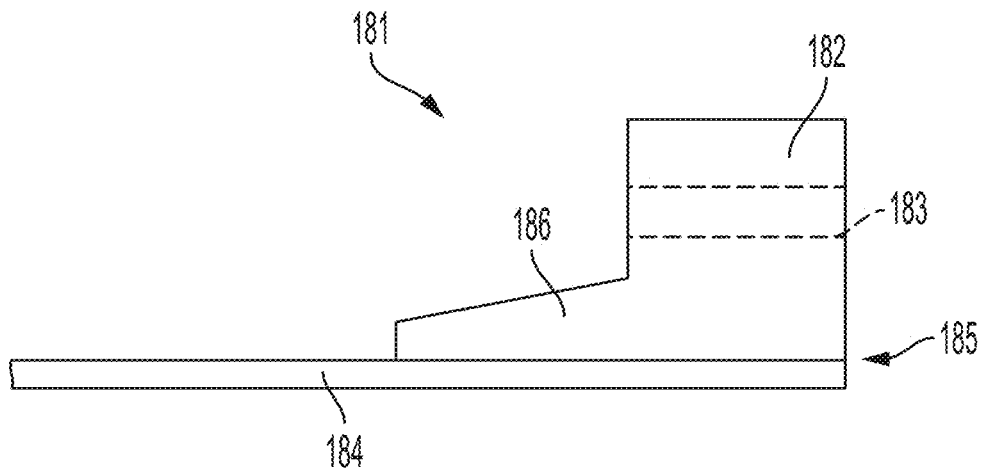
FIG. 19A illustrates a side cutaway view of an embodiment of a mesh strap attached to a lock-head.
Figure 19B:
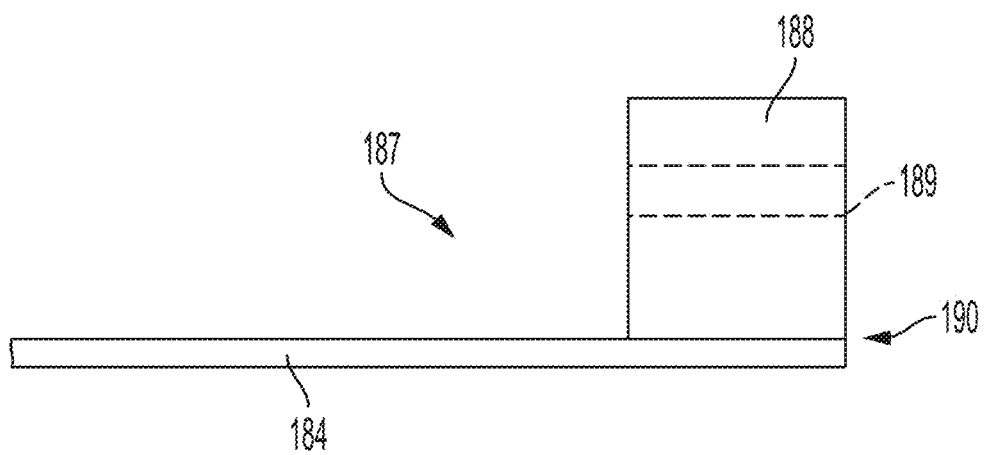
FIG. 19B illustrates a side cutaway view of an embodiment of a mesh strap attached to a lock-head.

In some embodiments, the strap 184 may be attached directly to the lock-head, as shown in FIGS. 19A-B, using any common techniques for joining two polymeric materials such as bonding, heat staking, ultrasonic welding, overmolding, etc. As shown in FIG. 19A, for example, the lock-head 182 comprising aperture 183 therethrough, has a tab 186 that provides a larger surface area for the strap 184 to attach onto; i.e., in this embodiment, the strap 184 attaches to the tab 186 at the base of the lock-head 182 through a relatively large attachment joint 185. FIG. 19B illustrates a lock-head 188, comprising aperture 189 therethrough, without the tab having a smaller overall size, but also a potentially a smaller attachment joint 190. One skilled in art will recognize that there are many ways to attach a flexible mesh to a small lock-head, for example, the mesh may be looped onto a feature, such as an aperture or hook, on the lock-head and tied into a knot, or crimped, or bonded onto the lock-head or crimped or bonded onto itself after passing through a loop-like feature on the lock-head so that it will not slip back through.

Figure 20A:
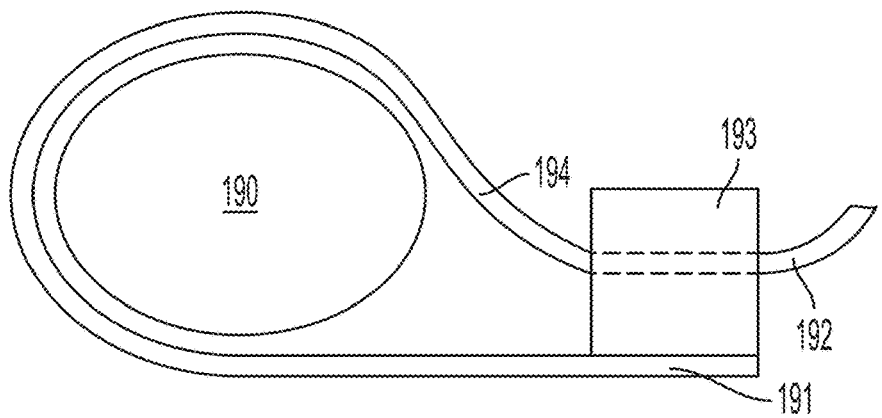
FIG. 20A illustrates an embodiment of lock-head and strap engagement arrangements.
Figure 20B:
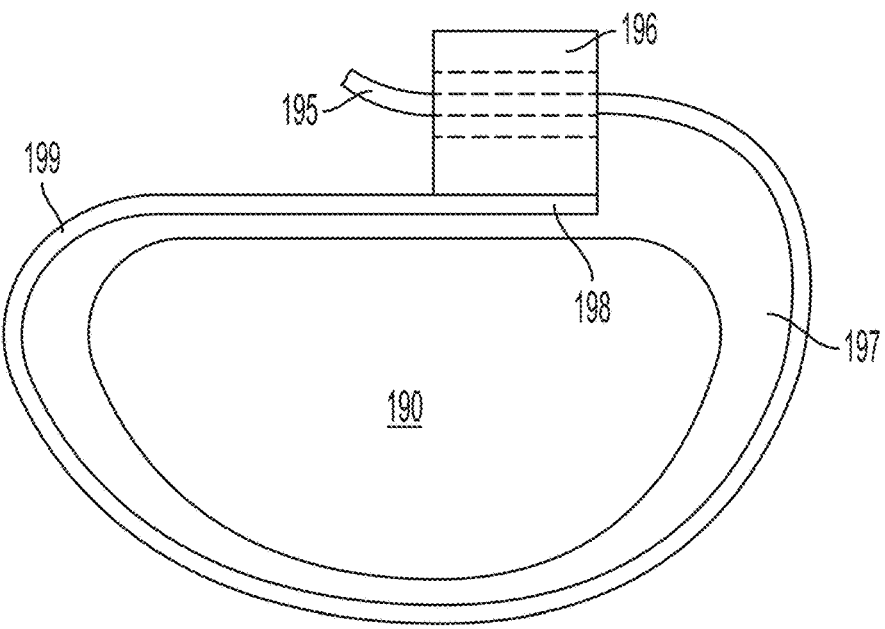
FIG. 20B illustrates an embodiment of lock-head and strap engagement arrangements.
Figure 20C:
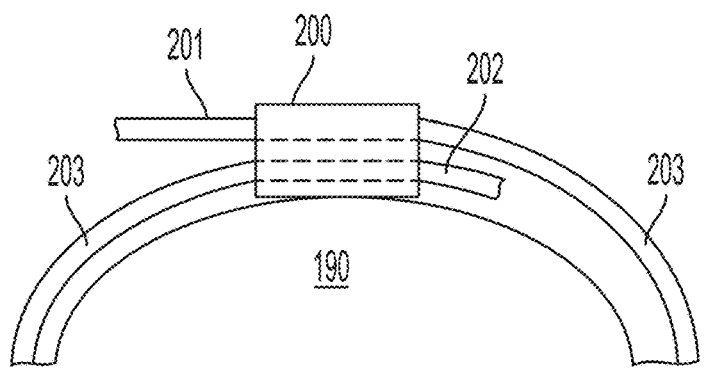
FIG. 20C illustrates an embodiment of lock-head and strap engagement arrangements.

Now with reference to FIGS. 20A-20C which illustrate different arrangements of a strap as it encircles around a tissue section 190 as shown in a cross-sectional view. Depending on the nature of the surgical procedure, different strap and lock-head arrangements may have certain advantages depending on the surgical procedure (inside vs. outside, open vs. closed and laparoscopic, etc.) and surgical tools used. In FIG. 20A, the lock-head 193 has a strap 194 attached to the base of the lock-head 193, and the strap 194 encircles the tissue 190 such that the distal end 192 of the strap 194 exits substantially in the same direction as the proximal end 191 of the strap 194. Alternatively, FIG. 20B shows an arrangement wherein the proximal end 198 of the strap 199 that is attached to the lock-head 196 is directed in the opposite direction from the proximal end 195 of the strap 199 as the strap encircles the tissue 190. Finally, as shown in FIG. 20C, in this embodiment, neither end of the strap 203 is attached to the outside of the lock-head 200; instead, the distal end 201 and the proximal end 202 passes through the lock-head 200 via one-way locking mechanisms. Alternatively, one or both ends of the strap 203 may be crimped into the lock-head 200. It should be noted that the lock-head sketches shown in the figures are for illustrative purposes and meant to demonstrate the main features and functionality. As such, they are shown in simple shapes. However, they may be shaped in much lower profile, streamlined, atraumatic shapes. Furthermore, the strap embodiments shown in FIGS. 20A-20B may alternatively be a one-piece plastic injection molded unit with the strap integrally attached to the lock-head but having the general strap engagement configuration as shown.

Figure 21:
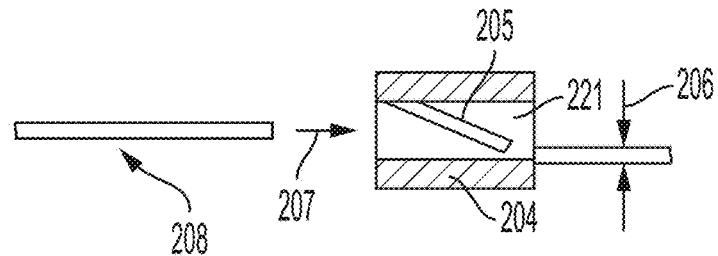
FIG. 21 illustrates a cross-sectional cutawy view of an embodiment of a lock-head having a cantilever beam.

The lock-head may comprise an aperture through which the strap passes, or translatingly moves relative to the lock-head, in one direction while being locked from passage, or translating movement relative to the lock-head, in the opposite direction. To achieve this locking action, the aperture may have teeth inside which dig into the mesh; the teeth may be metal teeth inserted into a plastic head, or metal teeth punched or otherwise formed in a metal lock-head. Alternatively, the teeth may be integrally molded into a plastic lock-head. Similarly, the lock-head may house barbs or similar one-way grasping features designed to snag on the mesh, thus providing one-way restriction. One example is shown in FIG. 21, which shows a cross-sectional view of a lock-head 204 having an angled tine 205 (e.g., beam or arm) in the aperture 221 through which the strap 208 passes. The strap can pass in the direction of arrow 207 but will be restricted in the opposite direction. The gap 206 between the tine 205 (beam or prong) may be the same thickness as the strap in its extended form, that is when it is being pulled through the aperture under tension. i.e., the strap may be flattened. This will provide low resistance while pulling through in the direction of the arrow 207. In designs where the gap 206 is lowered, the locking resistance will increase as well as the pull-through resistance in the direction of the arrow 207 that the operator perceives during use. In some embodiments, there may be no gap, that is, the gap 206 is zero such that the tine 205 contacts the body of the lock-head 204. Thus, when the strap 208 is pulled in the direction of the arrow 207, the tine 205 may flex to allow the strap 208 to pass through, but the tine has considerable stiffness when forced in the opposite direction due to its orientation, thus locking the strap 208 from travel in the direction opposite to the arrow 207.

Figure 22A:
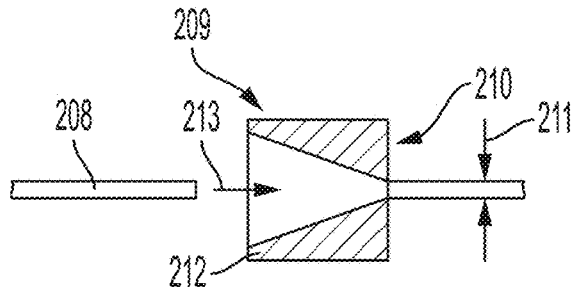
FIG. 22A illustrates a side, cross-sectional and cutaway view of an embodiment of a lock-head having an anulus suitable for a mesh or elastic strap.
Figure 22B:
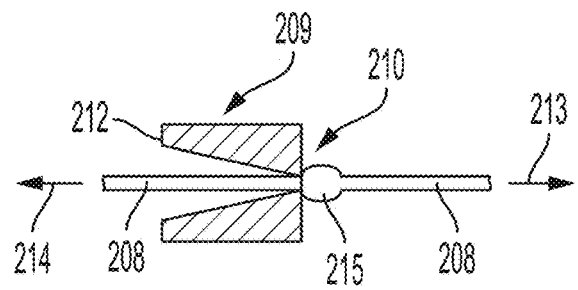
FIG. 22B illustrates a side, cross-sectional and cutaway view of an embodiment of a lock-head having an anulus suitable for a mesh or elastic strap.

Another type of locking mechanism is shown in FIGS. 22A-23B. FIG. 22A is a cross-sectional view of a lock-head 209 having an aperture that tapers from a wide opening 212 to a narrow exit 210 having a gap 211 that may be sized in a similar fashion as that described above in FIG. 21, except that if the gap 211 is zero, the exit 210 shall be flexible so as to deform enough to allow the strap 208 to pass through. In general, the exit 210 may be round like an annulus, or rectangular because the strap 208, being a flexible mesh structure, compresses or conforms as it passes through the lock-head 209 in the direction of the arrow 213. After the strap 208 is tensioned around an object, the strap 208 will be in tension in the opposite direction, indicated by the arrow 214. Because the lock-head 209 is tapered at the exit 210 in the reverse direction, the strap 208 tends to bunch up, causing a bulge 215 in the strap 208 at the exit 210, providing increased resistance to travel in the reverse direction. This behavior may also occur when the strap is elastic such that it is made of a rubber-like material that necks down under tension—i.e., elastic materials that are incompressible or nearly incompressible, such as rubber, elastomers, and thermoplastic elastomers. In some embodiments, the strap may be an elastic member and in other embodiments the elastic member may reside inside of a tubular mesh strap so that the strap is elastic along its length, but strengthened by an outer mesh. In such embodiments, the lock-head may not need to be tapered as an annulus will suffice so that when the elastic member is pulled through the lock-head in tension, it necks down; any annulus smaller than the undeformed diameter of the strap will tend to prevent loosening. A smaller annulus will generally provide a higher holding force while being more difficult for the operator to tighten.

An elastic strap will tend to continue applying force to tissue even if the tissue within the strap shrinks (loses bulk), whereas a rigid strape, such as a thermoplastic strap will tend to become lax if the encapsulated tissue shrinks after the surgery.

Figure 23A:
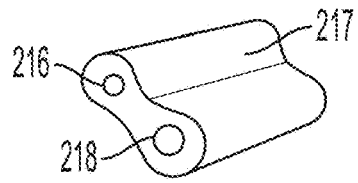
FIG. 23A illustrates a perspective view of an embodiment of an unattached lock-head suitable for a mesh or elastic strap.
Figure 23B:
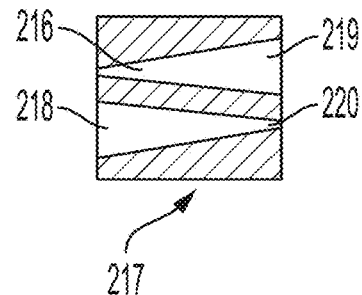
FIG. 23B illustrates a side cross-sectional view of an embodiment of an unattached lock-head suitable for a mesh or elastic strap.

In other embodiments, the strap may not be permanently joined to the lock-head at either end, as both ends may be clamped through the lock-head either during or before use. FIGS. 23A-B illustrate a lock-head 217 having a wide opening 218 and a narrow exit 220 and an oppositely oriented aperture with a wide opening 219 and narrow exit 216 arranged in the opposite direction. In general, in embodiments disclosed herein, the lock-head may be separate from the strap when provided to the operator; in these embodiments, both the distal and proximal ends of the strap may pass through the same or separate one-way locking features on a lock-head.

Figure 24:
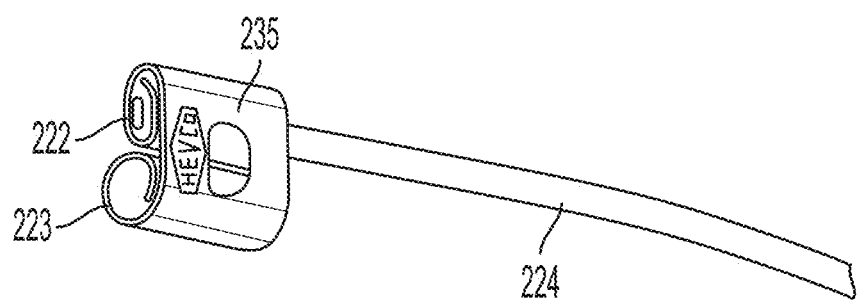
FIG. 24 illustrates a perspective cutaway view of an embodiment of a lock-head attachable by crimping.

In yet another embodiment, as shown in FIG. 24, the strap may be crimped in a malleable lock-head 235 that may be crushed around the strap 224. One end of the strap 224 may be pre-attached or crimped in a first channel 222, while the opposite end of the strap is be placed through a second channel 223, which is subsequently crushed during the procedure. The second channel 223 may be sized such that the strap 224 slides through with an interference fit such that the lock-head 235 stays in place during the procedure even before crushing the lock-head 235; this allows the wound to be gradually closed by applying multiple serially tightened straps along the defect.

Figure 25:
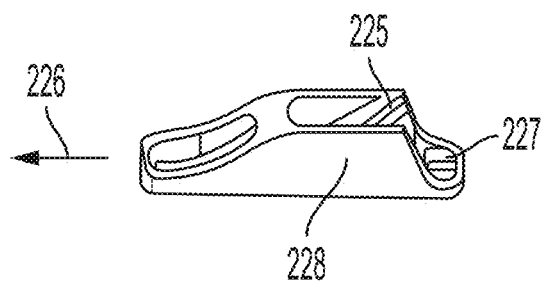
FIG. 25 illustrates a perspective view of an embodiment of a lock-head having a biased on-way lever.

In some embodiments, the strap may be secured by a cam mechanism using either a flexure or a hinging cam element. FIG. 25 shows a lock-head 228 having a lever 225 that is hinged such that when a strap enters through the entrance 227 of the lock-head, the lever 225 is forced open and allows the strap to pass through in the direction of the arrow 226. The cam is biased so that it compresses onto the strap. A flexing cam arm is essentially the same as the embodiment described above and shown in FIG. 21. Another type of lock-head embodiment having two cam elements is shown in FIG. 26 wherein the strap 229 passes between two opposing cam heads 230 and 231, which are biased to compress the strap between them. Finally, a lock-head 233 having a single cam element 232 is shown in FIGS. 27A-27B. This cam element 232 has a pivot 234, allowing the cam 232 to pinch the strap against the body of the lock-head; the cam 232 may have teeth as shown to facilitate grasping the strap. The teeth may catch on the strap when the strap has tension in the direction of the arrow 236, thus self-locking in that direction. A biasing spring may not be required if the size of the orifice through which the strap passes is small enough to guarantee engagement with the teeth. The strap will generally freely travel in the direction indicated by arrow 237.

Figure 28A:
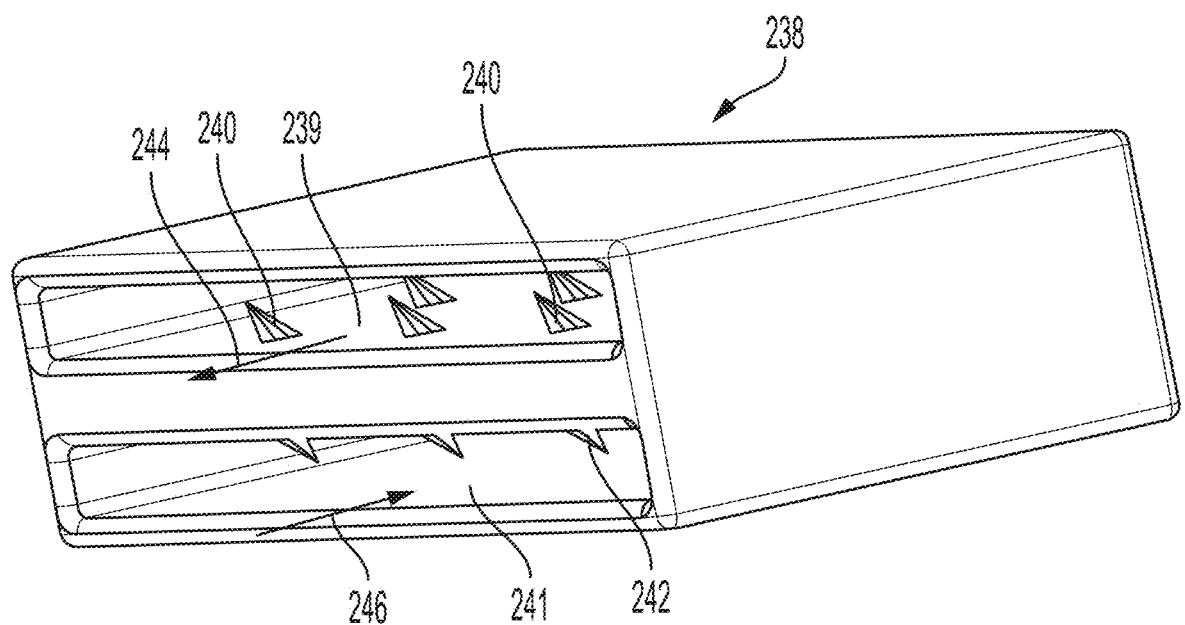
FIG. 28A illustrates a perspective view of an embodiment of a lock-head having teeth suitable for mesh or elastic straps.

Now with reference to FIG. 28A, a lock-head 238 having adjacent apertures 241 and 239 through which a strap passes. In addition to the strap embodiments previously described, strap may, alternatively, comprise a length of fabric, mesh or metallic mesh that extends at least partially along the strap length. Further, the leader may be a mesh or fabric that is overmolded (or otherwise combined) with soft plastic or elastomer that extends from both ends of the overmold section. These extensions may be introduced from opposite directions to create a one-way binding opposite the direction of being pulled. The overmold section remains flexible and provides the surface area to distribute the load over tissue mitigating the cheese wire effect of suture. The continuous integrated leader provides the tensile strength necessary to maintain closure of the tissue defect. The teeth penetrate and take hold of the mesh or fabric.

Figure 28B:
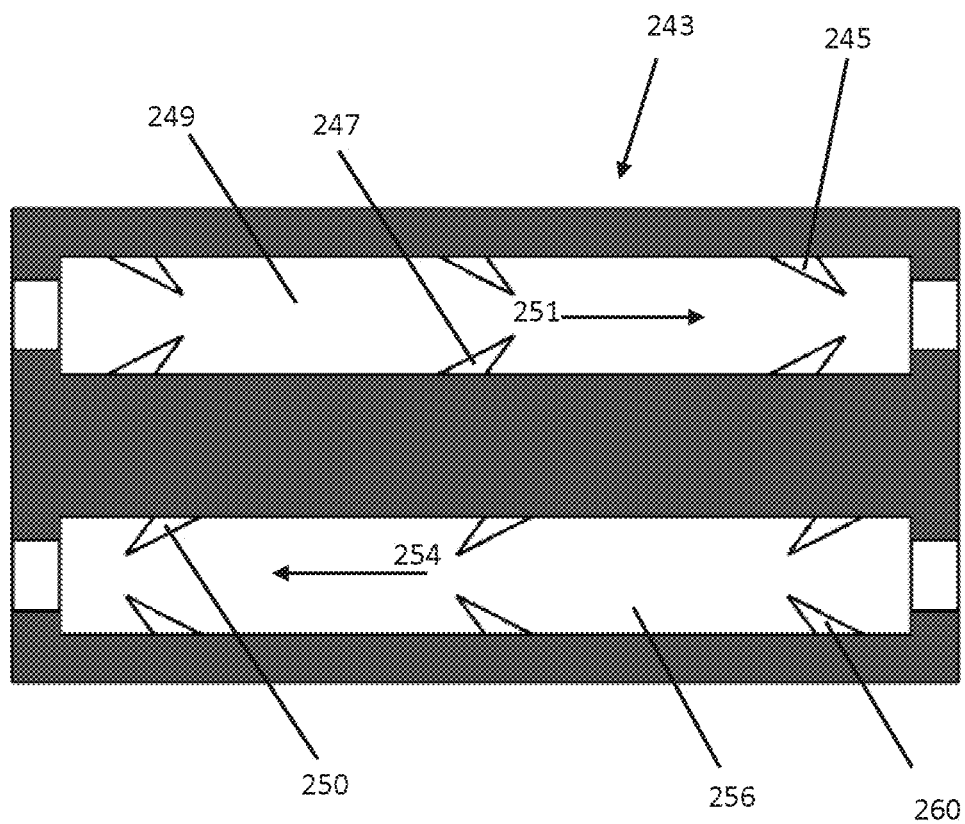
FIG. 28B illustrates a cross-sectional side view of an embodiment of a lock-head having teeth suitable for mesh or elastic straps.

Aperture 239 has teeth 240 canted in the direction of arrow 244, which is the direction that the strap comprising any of the strap embodiments described herein passes during tightening; thus, the strap is restricted from passing in the opposite direction because the teeth bite into it. Similarly, in the opposite aperture 241, the teeth 242 are pointing in the opposite direction 246, thus allowing the strap to pass in that direction. The teeth 240 and 242 may be molded into the head in the case of a polymeric head, or they may be formed via stamping or punching in a metal lock-head, or they may be embodied in a polymeric lock-head having a metal grip section. FIG. 28B illustrates a cross-section of an embodiment having teeth on both sides of each aperture; for example, the aperture 249 has teeth 245 on the upper side and teeth 247 on the lower side. Both sets are angled in the direction of the arrow 251 to allow passage in that direction while locking the displacement of the strap in the opposite direction. Similarly, the lower aperture 256 has teeth 250 on the upper side and teeth 260 on the lower side. Both sets are angled in the direction of the arrow 254 to allow passage in that direction while locking the displacement of the strap in the opposite direction. In each of these embodiments, the teeth may overlap. That is, they may be staggered on each side of the lock-head to reduce the effective size of the aperture, which may provide a stronger engagement. Furthermore, the teeth may be long enough to contact the opposite side of the aperture, relying on flex to allow the strap to pass through each aperture. The apertures may be oriented to pass the strap in the same direction, or there may be only one aperture while the opposite end of the strap is permanently attached to the lock-head.

Figure 29A:
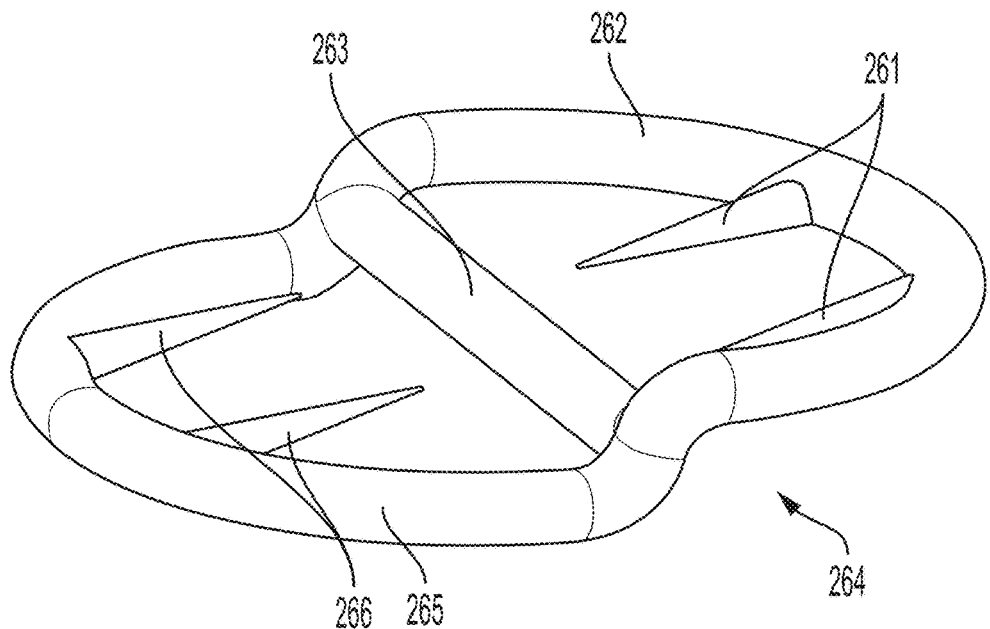
FIG. 29A illustrates a perspective view of an embodiment of a lock-head comprising a toothed-buckle.
Figure 29B:
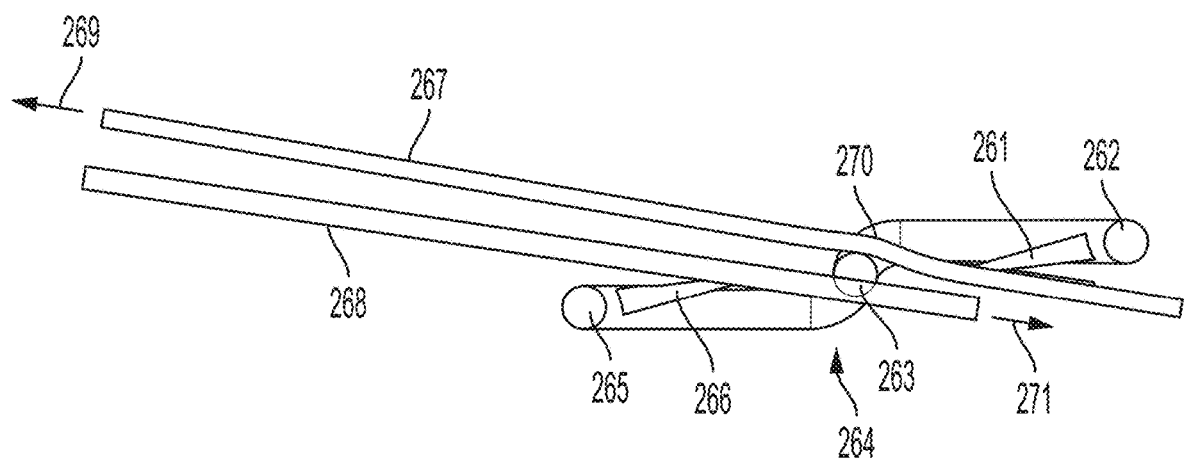
FIG. 29B illustrates a cross-sectional side cutaway view of an embodiment of a lock-head comprising a toothed-buckle.

FIGS. 29A-29B show a buckle-style lock-head 264 having a first loop 265 that may be offset from a second loop 262, however, the lock-head may operate similarly when the loops are in the same plane. Each loop has teeth 266 and 261, which pierce and restrain the strap when it is pulled opposite their direction. For example, as shown in FIG. 30B, the lower strap 268 can displace in the direction of the arrow 271, but is restricted in the opposite direction because it impinges on the teeth 266; it is restrained by the center shaft 263 so that it must impinge on the teeth 266. This is shown more specifically in the strap 267, which has a curve 279 as it is forced between the tooth 261 and the center shaft 263. Additionally, the teeth 261 and 266 may be canted downward, as shown, to create more interference with the straps 267 and 268, respectively. As noted in other embodiments, other versions of this embodiment may only have one strap locking loop while the other end of the strap may be permanently attached to the lock-head.

While the aforementioned lock-head embodiments were described in the context of attaching a mesh strap, one skilled in the art would recognize that these designs would also be applicable to a non-mesh strap, such as a smooth plastic or metal strap or an elastic strap.

In all of the aforementioned mesh strap embodiments, the leader may be made of the same material as the strap as a contiguous structure, and it may be narrower to facilitate passage through small apertures in the body. The reduced size may be accomplished by weaving, braiding, or other fabrication technique, or the leader may be heat-set to a smaller direction, or conversely, the strap section may be heat-set or expanded to a larger size. Alternatively, the leader may be a separate component from the strap and attached to the distal end of the strap by the methods described herein or by other methods for attaching a narrower leader to a relatively wider strap. In some embodiments, the leader may be a wire, suture, plastic strip, or mesh that is attached to the distal end of the mesh strap.

All of the embodiments disclosed herein may be provided with a needle attached to the distal end. The needle may be attached to the distal end of a strap or the distal end of a leader and serve to guide the device through tissue much like a suture with an attached needle. The leader or strap may be attached to the needle by any of the aforementioned methods for joining the leader to the strap or the strap to the lock-head, but the needle attachment methods are not limited to these approaches. Once the needle is passed through the desired tissue, any excess strap or leader length is cut off, which also removes the needle so that the strap may be placed through the lock-head for tightening.

Materials

The device embodiments described herein may be made of any material that can withstand the forces incurred in pulling the device through the body and the permanent implant (strap) should be capable of holding the tissue together without breaking or significantly yielding. Furthermore, as the strap is a permanent implant, it should be made of a material having long-term biocompatibility. Depending on the configuration of the embodiments described herein, the materials may be the same, for example, the lock-head, strap, and leader whether or not they are a contiguous structure or discrete elements that are joined in the manufacturing process, they may be made of the same material. Conversely, the device may be made of separate materials. For example, the leader and loop may be made of one material (e.g., Dacron), and the strap may be made of another (e.g., Nylon) Candidate materials include polymers or metals. Nonlimiting examples include Dacron, PEEK, PEKK, Nylon, polypropylene, polyethylene, polyethylene terephthalate, polyolefin, polyester (PET), any other common suture materials. Nonlimiting examples of metals include stainless steel and nitinol. For example, the leader may be made of a nitinol wire attached to a PEEK strap. Further, in some embodiments, at least portions of the devices described herein may comprise bioabsorbable materials.

The pre-bent or pre-curved sections of the leader 7, transition section 2 and/or strap 3 (when present) may be achieved by the use of a superelastic or shape material such as described above.

Further, the loop 9 may comprise a memory shape material that is biased to remain in the opened loop configuration as illustrated to help ensure that the loop 9 tends to remain open during the surgical procedure.

Figure 30A:
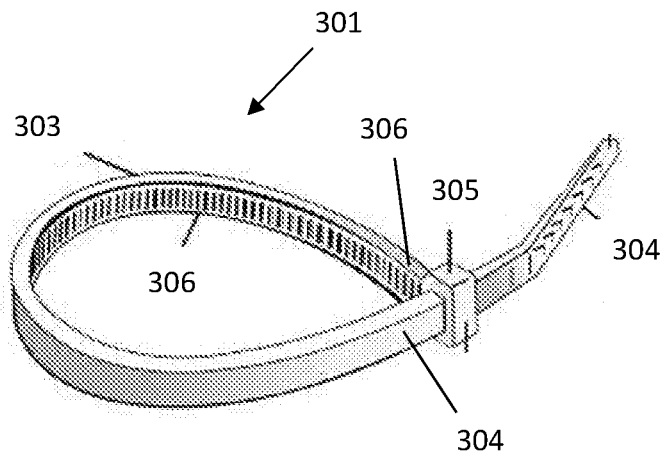
FIG. 30A illustrates a perspective view of one embodiment of a strap received within a lock-head.
Figure 30B:
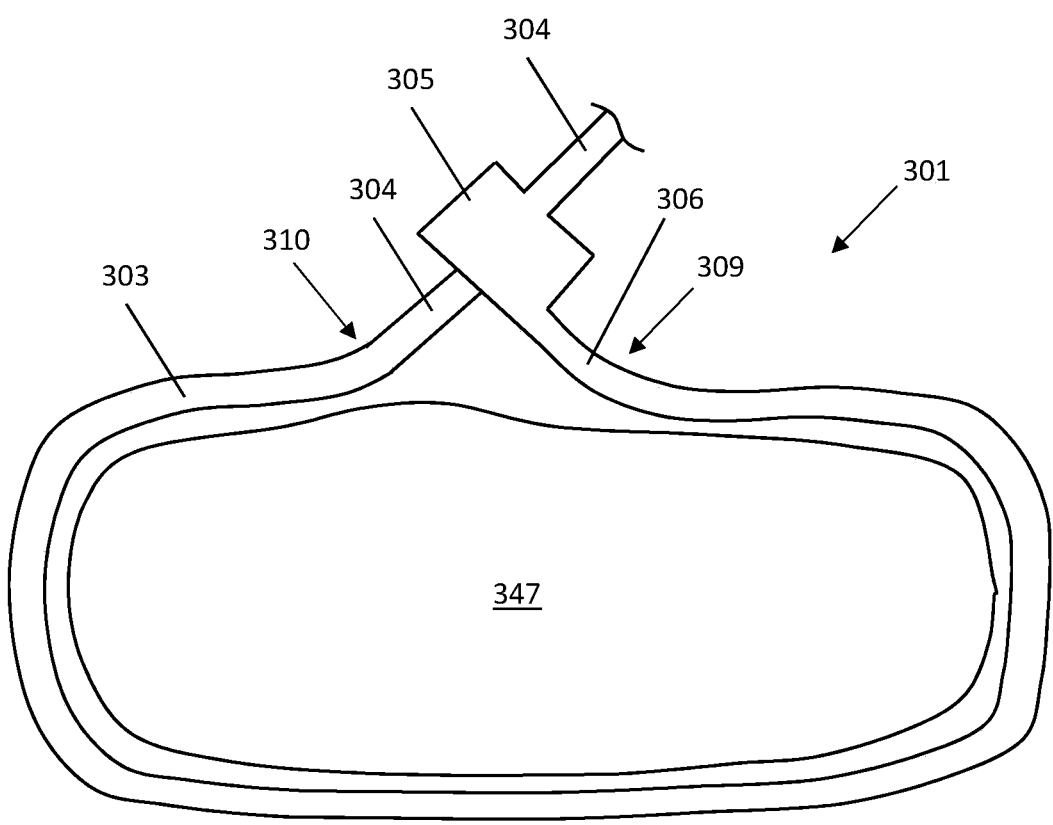
FIG. 30B illustrates the embodiment of FIG. 30A encircling tissue.

FIGS. 30A and 30B illustrate a strap embodiment having a lock-head that is substantially orthogonal to the strap. The device 301 is shown in a locked configuration in FIG. where the teeth 306 are oriented towards the inside of the loop; that is, near the tissue that is encircled. The lock-head 305 is arranged such that the proximal end 306 of the strap 303 is substantially orthogonal to the distal end 304 of the strap.

FIG. 30B shows this device 301 embodiment arranged around a cross-section of tissue 347. As the device 301 is tightened around the tissue 347, the strap 303 must curve to accommodate the orthogonal lock-head while tightening. For example, the proximal end 306 and the distal end 304 of the strap 303 incur bends 309 and 310, respectively, so that the distal end 304 may pass through the lock-head 305. The bends 309 and 310 generally become sharper (lower radius) as the device 301 is tightened on the tissue 347 resulting in increasing bending and particularly increased tensile stress locally which may reduce the holding strength of the device 301.

In some procedures, the device 301 may, however, be installed in the anatomy such that the orthogonal lock-head arrangement does not necessarily create bends near the lock-head. For example, and with reference to FIG. 30C, the device 301 is arranged around the tissue 347 such that the lock-head 305 resides near a side of the tissue 347 rather than in the mid-section of the tissue 347 as previously shown in FIG. 30B. Thus, the proximal end 306 and the distal end 304 of the strap 303 meet at an approximately orthogonal angle which is amenable to the lock-head 305 having an orthogonal aperture for receiving the distal end 304 of the strap 303.

Figure 31A:
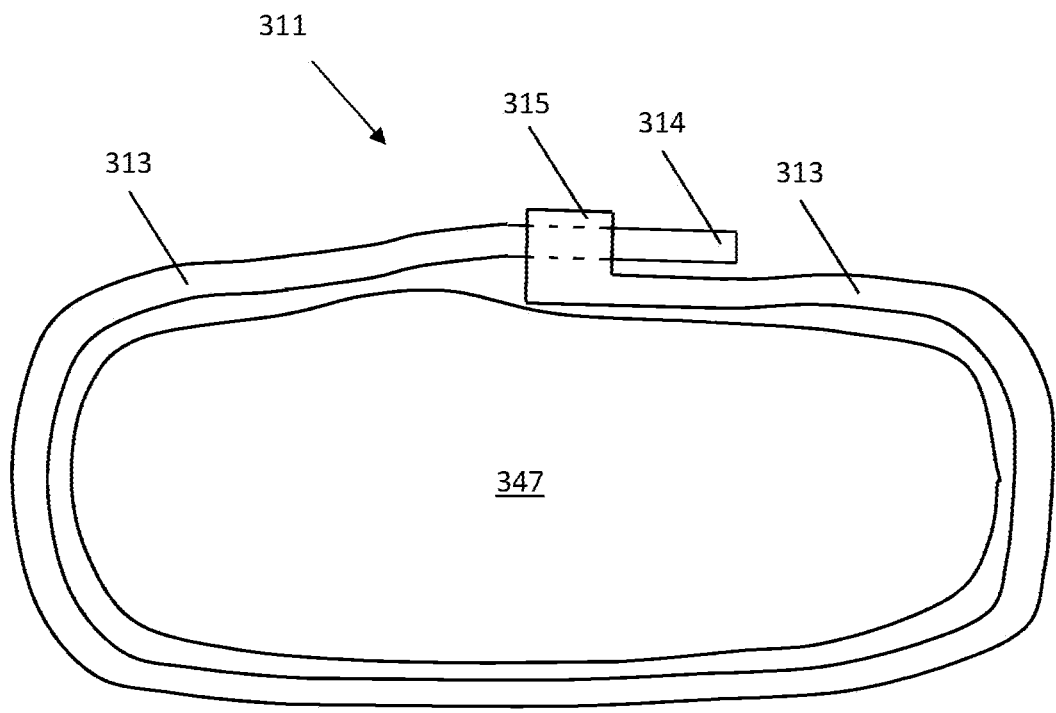
FIG. 31A illustrates an embodiment of a device with a lock-head having teeth for grasping a strap and permitting one-way directional translation of the strap through the lock-head.
Figure 31B:
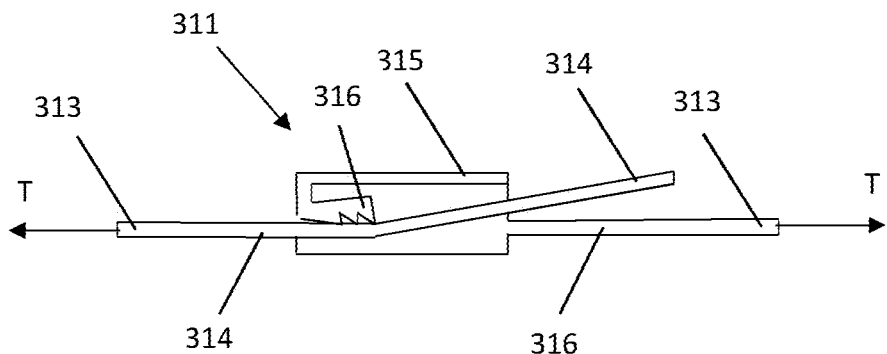
FIG. 31B illustrates the embodiment of FIG. 31A in a side view.

FIGS. 31A and 31B show an embodiment of a device 311 having a lock-head 315 with teeth 316 for grasping the strap 313 and permitting motion in one-direction only. In this embodiment, the distal end 314 of the strap 313 is substantially parallel to the proximal end 313 of the strap as the distal end 314 of the strap 313 passes through the lock-head 315. The tension as indicated by arrows "T" is substantially aligned throughout the force path through the lock-head 315 so that minimal bending stresses are added to the tension in the device 311.

Figure 32:
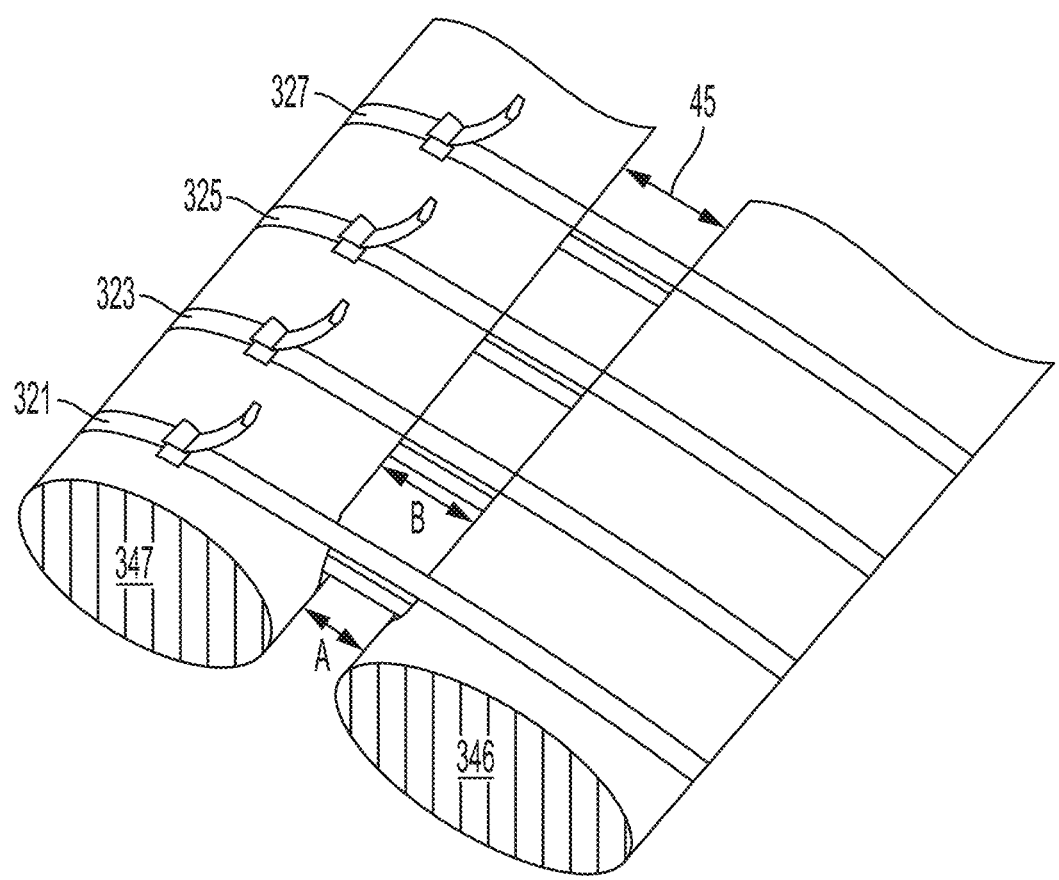
FIG. 32 illustrates an exemplary surgical system, device and method for approximating or closing a ventral hernia.

Self-locking straps are capable of staying in place, hands-free, once the strap is engaged with the lock-head, allowing the surgeon to attend to other tasks such as to tighten other straps. This enables serial tensioning without requiring knots or clamps. For example, FIG. 32 shows a ventral hernia procedure in the midst of serial tensioning using four self-locking straps. The right abdominus rectus muscle 346 is separated from the left abdominus rectus muscle 347 by the defect 45. In this scenario, the surgeon is closing the defect incrementally by tightening each strap 321, 323, 325, 327 in a desired order. As shown in FIG. 32, the straps 321, 323, 325, and 327 are locked in place. Notably, the superior end of the defect 45 has a gap "A" that is less than the gap "B," which exists throughout the remainder of the defect 45. This is because, in this example, the surgeon has tightened strap 321 incrementally more than the others, thus reducing the defect 45 locally. This technique of gradually reducing the defect 45 tends to reduce the interoperative force on the tissue, which may prevent local tearing or excessive subsidence of the strap into the tissue. The surgeon may proceed to tension the straps sequentially, that is from 321 to 323 to 325 to 327, or in any order based on surgeon preference. For example, the surgeon may skip a strap when tightening incrementally, or he may tighten the straps in the middle (323 and 325) more so than those on the ends (321 and 327) if the defect is larger in the middle. Any number of straps may be used depending on the length of the defect 45 and the degree of separation between the muscle tissues, among other factors. In some embodiments, a surgeon may space serially tightened straps approximately 1 cm apart along a defect such that a 10 cm defect will have 8-10 straps depending on the starting and finishing point along the defect.

Exemplary systems, devices and/or methods according to the disclosure herein comprise at least the following:

Embodiment 1: A method for tensioning a soft tissue defect, comprising:
  providing a first device, wherein the strap comprises a first strap having a proximal end and a distal end;

placing the distal end of the first strap through a first hole on a first side of the defect in soft tissue and into a body cavity;

pulling the distal end of the first strap through a second hole in the soft tissue on an opposite side of the defect;

pulling the distal end of the first strap through the first hole;

passing the distal end of the first strap through the lock-head; and tightening the first strap by translating the first strap a distance through the lock-head in one direction, wherein the lock-head prevents translational movement of the first strap in the opposite direction.

Embodiment 2: The method of embodiment 1, wherein the tightening of the first strap closes the soft tissue defect.

Embodiment 3: The method of embodiment 1, wherein the tightening of the first strap results in an incremental closure of the soft tissue defect.

Embodiment 4: The method of embodiment 3, further comprising repeating the tightening of the first strap in at least one additional incremental closure of the soft tissue defect until the soft tissue defect is closed.

Embodiment 5: The method of embodiment 1, further comprising providing a second device, the second device comprising a second strap having a proximal end and a distal end;

placing the distal end of the second strap through a third hole on the first side of the defect in soft tissue and into a body cavity, the second strap engaging the first side of the defect in soft tissue at a spaced apart location relative to the first strap;

pulling the distal end of the second strap through a fourth hole in the soft tissue on an opposite side of the defect, the second strap engaging the second side of the defect in soft tissue at a spaced apart location relative to the first strap;

pulling the distal end of the second strap through third hole;

passing the distal end of the second strap through a lock-head on the second strap; and tightening the second strap by translating the second strap a distance through a lock-head in one direction, wherein the lock-head prevents translational movement of the second strap in the opposite direction.

Embodiment 6: The method of embodiment 5, wherein the tightening of the first strap and the second strap results in closure of the soft tissue defect.

Embodiment 7: The method of embodiment 5, wherein the tightening of the first strap results in an incremental closure of the soft tissue defect.

Embodiment 8: The method of embodiment 7, wherein tightening of the second strap results in an incremental closure of the soft tissue defect.

Embodiment 9: The method of embodiment 8, further comprising repeating the tightening of the first strap and the tightening of the second strap until the soft tissue defect is closed.

Embodiment 10: The method of embodiment 9, wherein the repeated tightening of the first strap and the second strap is achieved in one or more incremental steps to gradually close the soft tissue defect.

Embodiment 11: The method of embodiment 1, further comprising providing a third device, the third device comprising a third strap having a proximal end and a distal end;

placing the distal end of the third strap through a fifth hole on the first side of the defect in soft tissue and into a body cavity, the third strap engaging the first side of the defect in soft tissue at a spaced apart location relative to the first strap and the second strap;

pulling the distal end of the third strap through a sixth hole the soft tissue on an opposite side of the defect, the third strap engaging the second side of the defect in soft tissue at a spaced apart location relative to the first strap and the second strap;

pulling the distal end of the third strap through first hole;

passing the distal end of the third strap through a lock-head on the third strap; and tightening the third strap by translating the third strap a distance through the lock-head in one direction, wherein the lock-head prevents translational movement of the third strap in the opposite direction.

Embodiment 12: The method of embodiment 11, wherein the tightening of the first strap and the second strap and the third strap results in closure of the soft tissue defect.

Embodiment 13: The method of embodiment 11, wherein the tightening of the first strap, the tightening of the second strap and the tightening of the third strap results in an incremental closure of the soft tissue defect.

Embodiment 14: The method of embodiment 13, further comprising repeating the tightening of the first strap and the tightening of the second strap and the tightening of the third strap until the soft tissue defect is closed.

Embodiment 15: The method of embodiment 14, wherein the repeated tightening of the first strap, the second strap and the third strap is achieved in one or more incremental steps to gradually close the soft tissue defect.

Embodiment 16: The method of embodiment 11, further comprising providing a fourth device, the fourth device comprising a fourth strap having a proximal end and a distal end;

placing the distal end of the fourth strap through a seventh hole on the first side of the defect in soft tissue and into a body cavity, the fourth strap engaging the first side of the defect in soft tissue at a spaced apart location relative to the first strap and the second strap and the third strap;

pulling the distal end of the fourth strap through an eighth hole in the soft tissue on an opposite side of the defect, the fourth strap engaging the second side of the defect in soft tissue at a spaced apart location relative to the first strap and the second strap and the third strap;

pulling the distal end of the fourth strap through first hole;

passing the distal end of the fourth strap through the lock-head on the fourth strap; and tightening the fourth strap by translating the fourth strap a distance through the lock-head in one direction, wherein the lock-head prevents translational movement of the fourth strap in the opposite direction.

Embodiment 17: The method of embodiment 16, wherein the tightening of the first strap, the tightening of the second strap, the tightening of the third strap and the tightening of the fourth strap results in closure of the soft tissue defect.

Embodiment 18: The method of embodiment 16, wherein the tightening of the first strap, the tightening of the second strap, the tightening of the third strap and the tightening of the fourth strap results in an incremental closure of the soft tissue defect.

Embodiment 19: The method of embodiment 18, further comprising repeating the tightening of the first strap and the tightening of the second strap, the tightening of the third strap and the tightening of the fourth strap until the soft tissue defect is closed.

Embodiment 20: The method of embodiment 19, wherein the repeated tightening of the first strap, the second strap, the third strap and the fourth strap is achieved in one or more incremental steps to gradually close the soft tissue defect.

Dimensions

The devices disclosed herein may lack radial symmetry. That is, they may be flat or rectangular in shape such that the larger area increases the contact area with the tissue to lower the stress on the tissue, as compared, for example, to a suture which has a small diameter and may cut through muscle tissue. In some embodiments, the straps may comprise cross-sectional shapes (e.g., flat, elliptical, etc.) that reduce tension against the tissue at the puncture site and reduce the likelihood of tissue tear. In some embodiments, the strap may reduce stress concentration where the strap contacts tissue. In some embodiments, a first cross-sectional dimension of the strap is greater than the orthogonal cross-sectional dimension, and the leader is smaller than the largest dimension of the strap and may be smaller than the smaller dimension of the strap. For example, the strap cross-sectional dimensions may be 2.5 mm×1.2 mm. The leader may be a suture, such as an 0 Prolene suture having a diameter of about 0.35 mm, or it may be a suture having another size, for example, between 0.35 and 0.6 mm in diameter. In other embodiments, the leader may be a tubular structure such as a woven Dacron braid having a diameter of approximately 0.7 mm.

In some embodiments, straps of the present invention provide various improvements over conventional sutures. In some embodiments, straps provide reduced likelihood of suture pull-through, increased closure strength, decreased number of straps for a closure, more rapid healing times, or reduction in closure failure relative to a traditional suture. Additionally, devices disclosed in the present invention provide knotless, self-locking ability for easy incremental tightening. That is, an array of self-locking strap devices may be placed along a hernia defect and tightened incrementally since the one-way locking mechanism holds the tissue in place hands-free and without requiring knots or clamps on the surgical field.

In some embodiments, the edge of the strap may be configured to contact the tissue or place pressure against the tissue to evenly distribute forces across the region of contact. For example, the strap shape may be convex such that it more evenly distributes force along a segment of tissue, rather than focusing it at a single point.

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A medical device configured to close a soft tissue defect, the device comprising:
    an elongate body having a strap at a proximal end, a leader at a distal end, and a transition section joining the strap to the leader;
    wherein the leader has a lower bending stiffness than the strap,
    wherein the leader comprises a different material than the strap,
    wherein the leader comprises a mesh,
    wherein the stiffness of the transition section gradually decreases from the strap to the leader; and
    a lock-head disposed at the proximal end of the strap, the lock-head having an aperture for receiving the distal end of the strap, the aperture configured for permitting at least one controlled translation of the strap in one direction through the lock-head and restricting motion in the opposite direction, wherein the controlled translation comprises a tightening of the strap.

2. The medical device of claim 1 wherein the leader has a smaller cross-sectional area and/or diameter than a cross-sectional area and/or diameter of the strap and the transition section tapers from the larger strap cross-sectional area and/or diameter to the smaller leader cross-sectional area and/or diameter.

3. The medical device of claim 2, wherein the cross-sectional diameter of the leader matches the smaller cross-sectional diameter of the transition section.

4. The medical device of claim 2, wherein the cross-sectional diameter of the strap matches the larger cross-sectional diameter of the transition section.

5. The medical device of claim 1, wherein the leader comprises a tubular shape.

6. The medical device of claim 1, wherein the leader, the strap and/or the transition section is made of one or more materials selected from a group consisting of Nylon, PEEK, polyester, polyethylene, polypropylene, Dacron, an elastomeric material, and bioabsorbable materials.

7. The medical device of claim 1 wherein the leader is a suture.

8. The medical device of claim 1, wherein the leader comprises at least one loop formed from a distal portion of the leader.

9. The medical device of claim 8, wherein the at least one loop comprises a stiffness that is greater than the stiffness of the rest of the leader.

10. The medical device of claim 1, comprising a stiffening element inside a lumen of at least a portion of the leader, the stiffening element comprising a monofilament.

11. The medical device of claim 10, wherein the leader comprises at least one loop formed from a distal portion of the leader, the at least one loop comprising a stiffness that is greater than the stiffness of the rest of the leader, wherein the monofilament is disposed within at least a portion of the at least one loop.

12. The medical device of claim 1, wherein the aperture is oriented parallel to the strap, wherein the distal end of the strap resides substantially parallel to the proximal end of the strap when the strap is tightened.

13. The medical device of claim 1, wherein the transition section comprises a transition from the leader to the strap selected from the group consisting of a transition in size, a transition in shape, and a transition in material.

14. The medical device of claim 1 wherein the transition section has a smooth surface suitable for smooth passing through tight passages in tissue.

15. The medical device of claim 1, wherein the medical device comprises a single molded part.

16. The medical device of claim 1 wherein the strap comprises opposing sides and further comprises teeth arranged along at least a portion of at least one of the opposing sides.

17. The medical device of claim 16, wherein the teeth are arranged on both of the opposing sides.

18. The medical device of claim 17, wherein the teeth on one of the opposing sides are staggered relative to the teeth on the other opposing side.

19. The medical device of claim 1, wherein the strap comprises opposing sides and further comprises a plurality of sets of teeth, wherein each of the plurality of sets of teeth comprise at least one tooth and adjacent sets of teeth are spaced apart from each other by a gap.

20. The medical device of claim 1, wherein the strap comprises side rails that extend longitudinally along at least a portion of a length of the strap.

21. The medical device of claim 1, wherein the strap comprises at least one of the group consisting of a weave structure, a non-woven structure, a braid structure, and a knit structure.

22. The medical device of claim 1, wherein the strap is adapted to be tightened by controlled translation of the strap without any knots or clamps.

23. The medical device of claim 1, wherein the strap is adapted to be tightened in successive and separate, serial translations.

24. The medical device of claim 1, wherein at least a portion of at least one of the group consisting of the leader, the transition section, and the strap comprise a pre-curved section.

25. The medical device of claim 1, further comprising a needle attached to a distal end of the leader.

26. The medical device of claim 1, wherein the lock-head is affixed to the strap by one of bonding, crimping, over-molding, thermally bonding, and ultrasonic welding.

27. A medical device configured to close a soft tissue defect, the device comprising:
   an elongate body having a strap at a proximal end, a leader at a distal end, and a transition section joining the strap to the leader;
   a stiffening element inside a lumen of at least a portion of the leader,
   wherein the leader has a lower bending stiffness than the strap,
   wherein the leader comprises a different material than the strap,
   wherein the stiffness of the transition section gradually decreases from the strap to the leader; and
   a lock-head disposed at the proximal end of the strap, the lock-head having an aperture for receiving the distal end of the strap, the aperture configured for permitting at least one controlled translation of the strap in one direction through the lock-head and restricting motion in the opposite direction, wherein the controlled translation comprises a tightening of the strap.

28. The medical device of claim 27, wherein the leader comprises a mesh.

29. The medical device of claim 27, wherein the stiffening element comprises a shape memory material having super-elastic properties.

30. The medical device of claim 27, wherein the leader comprises at least one loop formed from a distal portion of the leader, the at least one loop comprising a stiffness that is greater than the stiffness of the rest of the leader, wherein the stiffening element is disposed within at least a portion of the at least one loop.

31. A medical device configured to close a soft tissue defect, the device comprising:
   an elongate body having a strap at a proximal end, a leader at a distal end, and a transition section joining the strap to the leader;
   wherein the strap comprises an elastomeric material,
   wherein the leader has a lower bending stiffness than the strap,
   wherein the leader comprises a different material than the strap,
   wherein the stiffness of the transition section gradually decreases from the strap to the leader; and
   a lock-head disposed at the proximal end of the strap, the lock-head having an aperture for receiving the distal end of the strap, the aperture configured for permitting at least one controlled translation of the strap in one direction through the lock-head and restricting motion in the opposite direction, wherein the controlled translation comprises a tightening of the strap.

32. A medical device configured to close a soft tissue defect, the device comprising:
   an elongate body having a strap at a proximal end, a leader at a distal end, and a transition section joining the strap to the leader;
   wherein at least a portion of the strap comprises a tubular structure wherein the leader has a lower bending stiffness than the strap,
   wherein the leader comprises a different material than the strap,
   wherein the stiffness of the transition section gradually decreases from the strap to the leader; and
   a lock-head disposed at the proximal end of the strap, the lock-head having an aperture for receiving the distal end of the strap, the aperture configured for permitting at least one controlled translation of the strap in one direction through the lock-head and restricting motion in the opposite direction, wherein the controlled translation comprises a tightening of the strap.

* * * * *